(12) United States Patent
Skiba et al.

(10) Patent No.: US 7,672,719 B2
(45) Date of Patent: Mar. 2, 2010

(54) BATTERIES AND METHODS OF MANUFACTURE AND USE

(75) Inventors: Jeffry B. Skiba, Chandler, AZ (US); Lawrence A. Schneider, Scottsdale, AZ (US)

(73) Assignee: Vomaris Innovations, Inc., Chandler, AZ (US)

( * ) Notice: Subject to any disclaimer, the term of this patent is extended or adjusted under 35 U.S.C. 154(b) by 1392 days.

(21) Appl. No.: 11/061,235

(22) Filed: Feb. 18, 2005

(65) Prior Publication Data

US 2005/0192636 A1 Sep. 1, 2005

Related U.S. Application Data

(63) Continuation-in-part of application No. 10/784,088, filed on Feb. 19, 2004.

(51) Int. Cl.
*A61N 1/00* (2006.01)

(52) U.S. Cl. .............................. 607/2; 607/1

(58) Field of Classification Search .............. 607/1–2
See application file for complete search history.

(56) References Cited

U.S. PATENT DOCUMENTS

| | | | |
|---|---|---|---|
| 116,562 A | 7/1871 | Collins |
| 167,162 A | 8/1875 | French |
| 175,974 A | 4/1876 | Hall |
| 222,276 A | 12/1879 | Hunter |
| 393,741 A | 12/1888 | Collins |
| 3,848,608 A | 11/1974 | Leonard |
| 4,034,750 A | 7/1977 | Seiderman |
| 4,142,521 A | 3/1979 | Konikoff |
| 4,211,222 A | 7/1980 | Tapper |
| 4,528,265 A | 7/1985 | Becker |
| 4,529,623 A | 7/1985 | Maggs |
| 4,540,604 A | 9/1985 | Siuta |
| 4,569,673 A | 2/1986 | Tesi |
| 4,585,652 A | 4/1986 | Miller et al. |
| 4,657,808 A | 4/1987 | Maggs |
| 4,767,401 A | 8/1988 | Seiderman |
| 4,817,594 A | 4/1989 | Juhasz |

(Continued)

FOREIGN PATENT DOCUMENTS

GB 1588933 4/1981

(Continued)

OTHER PUBLICATIONS

"A powerful combination for the care of chronic wounds", http://www.jnjgateway.com/home.jhtml?loc=USENG&page=viewContent&contentId=090..., (Observed Jan. 13, 2005),2 pages.

(Continued)

*Primary Examiner*—Carl H Layno
*Assistant Examiner*—Deborah Malamud
(74) *Attorney, Agent, or Firm*—Meschkow & Gresham, PLC

(57) ABSTRACT

An apparatus includes multiple first reservoirs and multiple second reservoirs joined with a substrate. Selected ones of the multiple first reservoirs include a reducing agent, and first reservoir surfaces of selected ones of the multiple first reservoirs are proximate to a first substrate surface. Selected ones of the multiple second reservoirs include an oxidizing agent, and second reservoir surfaces of selected ones of the multiple second reservoirs are proximate to the first substrate surface.

5 Claims, 18 Drawing Sheets

U.S. PATENT DOCUMENTS

| | | | |
|---|---|---|---|
| 4,937,323 A | 6/1990 | Silver et al. | |
| 5,053,001 A | 10/1991 | Reller et al. | |
| 5,143,079 A | 9/1992 | Frei et al. | |
| 5,288,289 A | 2/1994 | Haak et al. | |
| 5,298,017 A | 3/1994 | Theeuwes et al. | |
| 5,322,520 A | 6/1994 | Milder | |
| 5,352,315 A | 10/1994 | Carrier et al. | |
| 5,360,440 A | 11/1994 | Andersen | |
| 5,405,317 A | 4/1995 | Myers | |
| 5,454,886 A | 10/1995 | Burrell et al. | |
| 5,681,575 A | 10/1997 | Burrell et al. | |
| 5,685,837 A | 11/1997 | Horstmann | |
| 5,695,857 A | 12/1997 | Burrell et al. | |
| 5,741,224 A | 4/1998 | Milder | |
| 5,753,251 A | 5/1998 | Burrell | |
| 5,759,564 A | 6/1998 | Milder | |
| 5,770,255 A | 6/1998 | Burrell et al. | |
| 5,772,688 A | 6/1998 | Muroki | |
| 5,782,788 A | 7/1998 | Widemire | |
| 5,814,094 A | 9/1998 | Becker | |
| 5,837,275 A | 11/1998 | Burrell et al. | |
| 5,855,570 A * | 1/1999 | Scherson et al. | 604/304 |
| 5,944,685 A | 8/1999 | Muroki | |
| 5,958,440 A | 9/1999 | Burrell et al. | |
| 5,974,344 A | 10/1999 | Shoemaker, II | |
| 5,985,308 A | 11/1999 | Burrell et al. | |
| 6,017,553 A | 1/2000 | Burrell et al. | |
| 6,038,485 A | 3/2000 | Axelgaard | |
| 6,080,490 A | 6/2000 | Burrell et al. | |
| 6,087,549 A | 7/2000 | Flick | |
| 6,181,963 B1 | 1/2001 | Chin et al. | |
| 6,238,686 B1 | 5/2001 | Burrell et al. | |
| 6,248,449 B1 | 6/2001 | Watanabe | |
| 6,306,419 B1 | 10/2001 | Vachon | |
| 6,333,093 B1 | 12/2001 | Burrell et al. | |
| 6,365,220 B1 | 4/2002 | Burrell et al. | |
| 6,522,918 B1 | 2/2003 | Crisp et al. | |
| 6,582,713 B2 | 6/2003 | Newell et al. | |
| 6,631,294 B2 | 10/2003 | Andino et al. | |
| 6,723,350 B2 | 4/2004 | Burrell et al. | |
| 6,738,662 B1 | 5/2004 | Frank | |
| 6,788,978 B2 | 9/2004 | Vesnaver | |
| 6,861,570 B1 | 3/2005 | Flick | |
| 2002/0004640 A1 | 1/2002 | Conn et al. | |
| 2002/0122787 A1 | 9/2002 | Newell et al. | |
| 2002/0161405 A1 | 10/2002 | Drake | |
| 2002/0182485 A1 | 12/2002 | Anderson et al. | |
| 2002/0188282 A1 | 12/2002 | Greenberg | |
| 2003/0144723 A1 | 7/2003 | Andino et al. | |
| 2004/0015223 A1 | 1/2004 | Andino et al. | |
| 2004/0030276 A1 | 2/2004 | Flick | |
| 2004/0049145 A1 | 3/2004 | Flick | |
| 2004/0059282 A1 | 3/2004 | Flock et al. | |
| 2004/0162602 A1 | 8/2004 | Cohen | |
| 2004/0167461 A1 | 8/2004 | Nitzan et al. | |
| 2004/0193089 A1 | 9/2004 | Fischer et al. | |
| 2004/0199086 A1 | 10/2004 | Crisp | |
| 2004/0265395 A1 | 12/2004 | Sun et al. | |
| 2004/0267169 A1 | 12/2004 | Sun et al. | |
| 2004/0267231 A1 | 12/2004 | Sun et al. | |
| 2004/0267232 A1 | 12/2004 | Sun et al. | |
| 2004/0267237 A1 | 12/2004 | Sun et al. | |
| 2005/0004506 A1 | 1/2005 | Gyory | |
| 2005/0004508 A1 | 1/2005 | Sun et al. | |
| 2005/0004509 A1 | 1/2005 | Sun et al. | |
| 2005/0004550 A1 | 1/2005 | Sun et al. | |
| 2005/0010161 A1 | 1/2005 | Sun et al. | |
| 2005/0010192 A1 | 1/2005 | Sun et al. | |
| 2005/0015042 A1 | 1/2005 | Sun et al. | |
| 2005/0085751 A1 | 4/2005 | Daskal et al. | |
| 2005/0125006 A1 | 6/2005 | Nady | |
| 2005/0125009 A1 | 6/2005 | Perry et al. | |
| 2005/0125012 A1 | 6/2005 | Houser et al. | |
| 2005/0125016 A1 | 6/2005 | Trerotola | |
| 2005/0125018 A1 | 6/2005 | Galloway et al. | |
| 2005/0125021 A1 | 6/2005 | Nance et al. | |
| 2005/0148996 A1 | 7/2005 | Sun et al. | |
| 2005/0187580 A1 | 8/2005 | Skiba | |
| 2005/0192636 A1 | 9/2005 | Skiba et al. | |
| 2006/0015052 A1 | 1/2006 | Crisp | |
| 2006/0015053 A1 | 1/2006 | Crisp | |
| 2006/0141015 A1 | 6/2006 | Tessier et al. | |

FOREIGN PATENT DOCUMENTS

| | | |
|---|---|---|
| JP | 03-080874 A2 | 4/1991 |
| WO | WO-0112157 A1 | 2/2001 |
| WO | WO-2004022033 A1 | 3/2004 |
| WO | WO-2005079913 A1 | 9/2005 |

OTHER PUBLICATIONS

"Managing chronic wounds", http://wound.smith-nephew.com/us/node.asp?NodeId=2871, (Observed Jan. 13, 2005),2 pages.

"Silver-Powered Antimicrobial Dressing", http://www.convatec.com/ag/us/index.html?ref=brandsite, (Observed Jan. 13, 2005),1 pages.

"Managing chronic wounds", http://wound.smith-nephew.com/us/node.asp?NodeId=2871, (Jan 13, 2005), 2 pages.

"Silver-Powered Antimicrobial Dressing", http://www.convatec.com/ag/us/index.html?ref=brandsite, (Jan. 13, 2005),1 page.

"International Search Report filed in corresponding PCT application No. PCT/US2005/005355", (Jun. 15, 2005), 8 pages.

* cited by examiner

BATTERIES AND METHODS OF MANUFACTURE AND USE

CROSS-REFERENCE TO RELATED APPLICATION

The present application is a continuation-in-part of co-pending U.S. patent application Ser. No. 10/784,088, filed Feb. 19, 2004, which is hereby incorporated by reference.

BACKGROUND

Biologic tissue, bacteria, viruses, fungi, and other organisms or organic matter may be affected by electrical stimulus. Accordingly, apparatus and techniques for applying electric stimulus to organic matter have been developed to address a number of medical issues.

BRIEF DESCRIPTION OF THE DRAWINGS

Like-reference numbers refer to similar items throughout the figures and.

DETAILED DESCRIPTION

Figure 1:
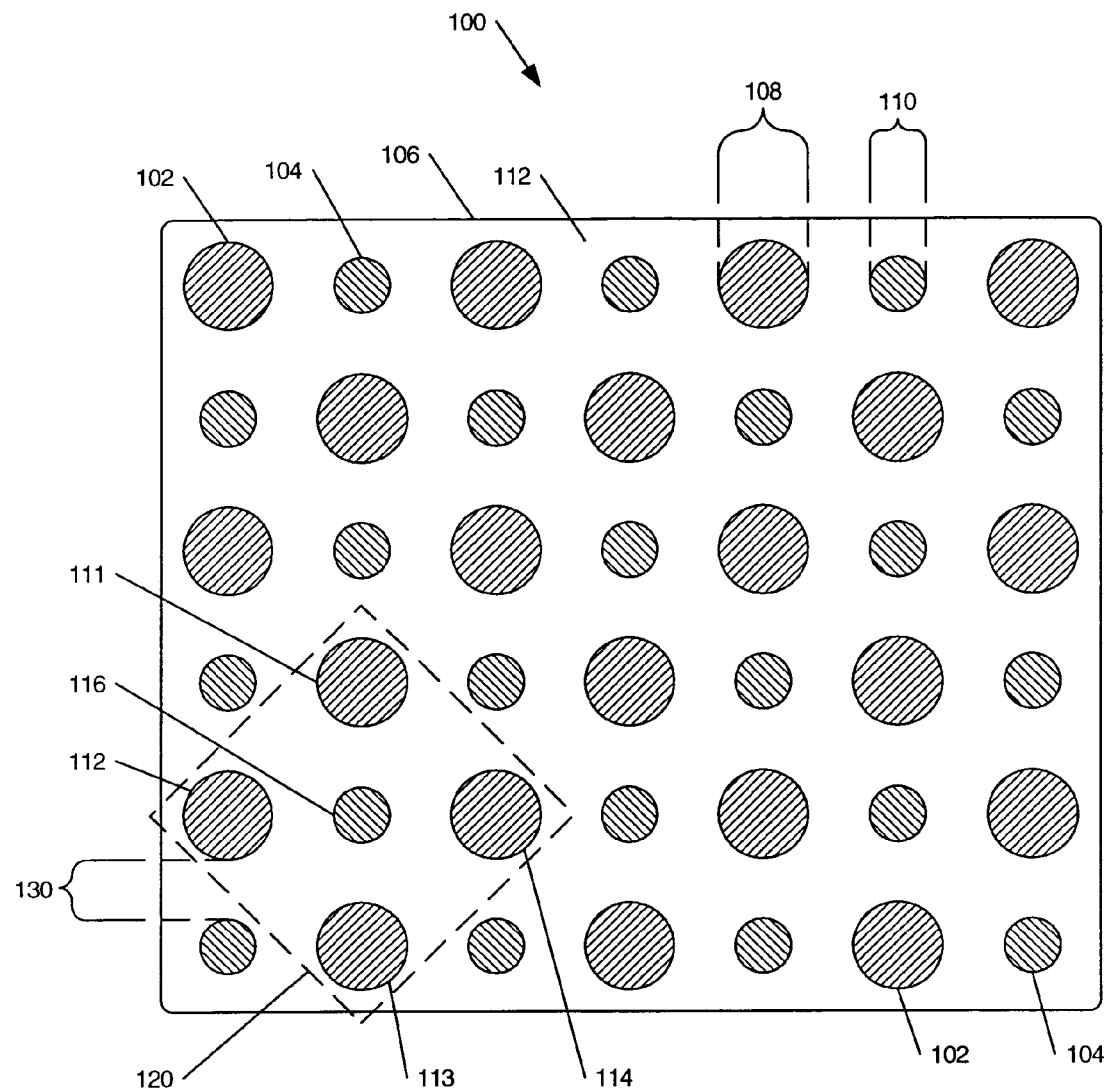
FIG. 1 is a top view of a medical battery having a first configuration of dissimilar reservoirs, in accordance with an example embodiment.

Various apparatus embodiments, which may be referred to as "medical batteries," are described herein. In addition, various embodiments of methods for manufacturing medical apparatus and methods for applying medical apparatus to "target tissue" are described herein. The term "medical battery" may be defined, in some embodiments, as apparatus that may, under certain circumstances, produce an electrical stimulus that may contact an area of "target tissue," and/or may electromotivate one or more therapeutic materials toward an area of target tissue (e.g., iontophoresis), and/or may cause one or more biologic or other materials within target tissue to be affected (e.g., attracted, killed, neutralized, etc.). The term "target tissue" includes, but is not limited to, human tissue, animal tissue, and plant tissue. "Tissue" may include, for example, but not by way of limitation, internal or external soft tissue and bone. Although the description, below, concentrates on application to and area of target tissue, it is to be understood that, during use, embodiments may produce effects in proximity to the target tissue and also, in some applications, systemically throughout one or more systems of an organism.

In various embodiments, an apparatus may include "discrete reservoirs," which may be joined with one or more substrates to form a medical battery. The term "discrete reservoir" may be defined, in some embodiments, as a mass of material, which has a boundary. The shape of a reservoir boundary may vary significantly, in various embodiments. Accordingly, although illustrated embodiments include reservoirs having various boundary configurations and cross-sectional shapes, it is to be understood that the inventive subject matter includes embodiments with reservoirs having other boundary configurations and cross-sectional shapes, as well. Further, although the term "substrate" may be used herein in a singular tense, it is to be understood that, in various embodiments, an apparatus may include a substrate having multiple interconnected or disjointed substrate surfaces. Accordingly, embodiments having multiple substrate surfaces are intended to be included within the scope of the inventive subject matter.

Embodiments described herein include, but are not limited to, medical batteries having two types of dissimilar reservoirs, where a reservoir of a first type may establish a first portion of a battery cell, and a reservoir of a second type may establish a second portion of a battery cell. In various embodiments, one or more reservoirs of a first type are configured with (e.g., positioned in spaced relation with) one or more reservoirs of a second, dissimilar type. The term "spaced relation" may be defined, in some embodiments, as having an orientation with respect to each other in space. The terms "dissimilar type" and "dissimilar reservoirs" may be defined, in some embodiments, as reservoirs having material compositions that differ in the materials included in the reservoirs and/or the proportions of materials included in the reservoirs.

It is to be understood that, in other embodiments, a medical battery may include reservoirs of only one type, or a medical battery may include reservoirs of more than two dissimilar types. In addition, it is to be understood that the illustrated embodiments are for example purposes, and accordingly medical batteries having different configurations of reservoirs from those illustrated herein are intended to be included within the scope of the inventive subject matter. Accordingly, it is to be understood that the illustrated embodiments are for the purpose of example, and should not be construed to limit the scope of the inventive subject matter to those illustrated embodiments.

It is to be understood that the use of oppositely-oriented cross-hatching in the Figures, in conjunction with first and second reservoirs, is not meant to imply that the first and second reservoirs are formed from or include conductive metals, although either or both may be formed from or include conductive metals. Instead, the use of oppositely-oriented cross-hatching in the Figures is used to indicate that the reservoirs are dissimilar.

FIG. 1 is a top view of a medical battery 100 having a first configuration of dissimilar reservoirs, in accordance with an example embodiment. In particular, battery 100 includes multiple first discrete reservoirs 102 and multiple second discrete reservoirs 104 joined with a substrate 106. Various materials that may be used to form first discrete reservoirs, second discrete reservoirs, a substrate, and other portions of a medical battery are described later.

As illustrated in FIG. 1, first reservoirs 102 and second reservoirs 104 may have substantially circular, solid shapes (e.g., when viewed from above, as shown). In other embodiments, either or both of first and second reservoirs may have alternative shapes, including but not limited to square, rectangular, elliptical, hexagonal, substantially linear, substantially planar, spiral, disc-like, open-centered, cross, letters, numbers, symbols, irregular shapes, and/or other shapes.

In an embodiment, first reservoirs 102 may have diameters 108 (or widths) of approximately 2 mm, and second reservoirs 104 may have diameters 110 (or widths) of approximately 1 mm. In other embodiments, either or both first reservoirs 102 and/or second reservoirs 104 may have one or more dimensions (e.g., height, diameter, width, length) that are greater or smaller than the above-given values. Reservoirs dimensions may, in various embodiments, be significantly smaller than the above-given values. For example, an apparatus may include "nano-reservoirs," which may have dimensions measurable on a nanometer (nm) scale (e.g., from approximately 1 nm to approximately 10,000 nm or more). Further, first reservoirs 102 and second reservoirs 104 may be of a similar size and shape, or their sizes and/or shapes may be substantially different from each other.

The material concentrations or quantities within and/or the relative sizes (e.g., dimensions or surface area) of the first and second reservoirs may be selected deliberately to achieve various characteristics of the apparatus' operational behavior. For example, the quantities of material within a first and second reservoir may be selected to provide a medical battery that depletes at approximately a desired rate and/or that "dies" after an approximate period of time after activation. In an embodiment, the one or more first reservoirs and the one or more second reservoirs are configured to sustain one or more currents for an approximate pre-determined period of time, after activation.

In various embodiments, materials within the first reservoirs and/or the second reservoirs may gradually deplete, after activation of the apparatus. For example, in an embodiment, a first reservoir may include silver and a second reservoir may include zinc. After activation of the apparatus, some or all of the silver and/or the zinc may gradually be expelled from its respective reservoir via electromotive force (e.g., iontophoresis), reservoir degradation, dissipation of the reservoir material, or otherwise. Alternatively or in addition, a voltage potential between the first and second reservoir may gradually decrease to near zero. When at least one of the galvanic materials has been depleted and/or the potential decreases significantly, redox reactions between the first and second reservoirs may eventually diminish and cease.

Certain reservoir materials may have therapeutic effects on the target tissue, and/or may result in other biologic activity, as will be described later. In some cases, it may be desirable to maintain therapeutic or other effects of one or more reservoir materials even after cessation of redox reactions between dissimilar reservoirs. Accordingly, a relative size of or material concentration within a first reservoir with respect to a second, dissimilar reservoir, may be selected so that the effects of the materials within the first reservoir continue beyond cessation of redox reactions. For example, a first reservoir may contain an amount of zinc and a second reservoir may contain an amount of silver. The amount of silver may be selected so that the silver is not completely depleted when redox reactions between the reservoirs have ceased, and accordingly therapeutic effects of the silver (e.g., anti-microbial effects) may continue. The reverse may also be the case (e.g., the zinc may not be completely depleted when the redox reactions have ceased).

In an embodiment, substrate 106 includes a top surface 112. Selected ones of the multiple first discrete reservoirs 102 are physically separated, across surface 112 of substrate 106, from selected ones of the multiple second discrete reservoirs 104, in an embodiment. Substrate 106 may form part of a substantially two-dimensional apparatus (e.g., an apparatus having width and height dimensions that are significantly greater than a depth dimension) or may form part of a substantially three-dimensional apparatus (e.g., an apparatus having width and height dimensions that are not significantly greater than a depth dimension), in various embodiments. In various embodiments, surface 112 may be substantially planar (e.g., flat). In other embodiments, substrate 106 may include a contoured and/or non-planar top surface. Substrate 106 and/or surface 112 may be rigid, or they may be moldable, bendable, and/or substantially conformable, in various embodiments.

In an embodiment, first discrete reservoirs 102 include first discrete reservoir surfaces "proximate to" top surface 112, and second discrete reservoirs 104 include second discrete reservoir surfaces proximate to top surface 112. The term "proximate to a surface" may be defined, in some embodiments, as having a positional relationship with respect to a surface, including positions above or slightly above, on, substantially flush with, below, or slightly below the surface. The term "proximate to a surface" may be defined, in other embodiments, as being located with respect to a surface so that electrical communication and/or ionic communication may be possible, for example, between dissimilar reservoirs. For example, but not by way of limitation, either or both of the first and second discrete reservoir surfaces may have a dome-like or puck-like shape, which extends above top surface 112. Alternatively, for example, but not by way of limitation, either or both of the first and second discrete reservoir surfaces may be exposed below the top surface 112 in depressions, holes or other openings.

Top surface 112 may be referred to herein as an "active surface." The term "active surface" may be defined, in some embodiments, as a substrate surface proximate to which electrical currents may be generated between dissimilar reservoirs in the presence of an electrically conductive material between the reservoirs. The term "current" includes a flow of charge per unit time (e.g., $I=dQ/dt$, where I is current, Q is charge, and t is time).

An active surface may or may not be a "tissue contacting surface," in various embodiments. A "tissue contacting surface" may be defined, in some embodiments, as a material surface, which during use, contacts an area of target tissue. For example, in an embodiment, top surface 112 may directly contact an area of target tissue during use of the apparatus, and accordingly, top surface 112 may function as both an active surface and a tissue contacting surface. In another embodiment, one or more additional materials may be included above top surface 112, and during use of the apparatus, a surface of one or more of the additional materials may function as a tissue contacting surface. Accordingly, in such an embodiment, the active surface and the tissue contacting surface may be different surfaces. A tissue contacting surface may include, for example but not by way of limitation, a layer of material and/or a solid, semi-solid, liquid, or gaseous conductive material.

The multiple first reservoirs 102 may form a portion of a first reservoir pattern, and the multiple second reservoirs 104 may form a portion of a second reservoir pattern, in an embodiment. The first reservoir pattern may be interleaved with the second reservoir pattern, in various embodiments. Either or both the first reservoir pattern and the second reservoir pattern may be consistent across a surface of substrate 106, as shown, or may have varying pattern densities. A pattern "density" may be defined, in some embodiments, as the number of reservoirs present per unit surface area. For example, but not by way of limitation, an apparatus may have variable pattern density (e.g., one or more relatively high pattern density areas and/or low pattern density areas). In FIG. 1, a pattern of twenty-one first reservoirs 102 and twenty-one second reservoirs 104 are illustrated. In alternative embodiments, more or fewer first and/or second reservoirs may be included in an apparatus.

In an embodiment, a first discrete reservoir 102 may be "adjacent to" one or more second discrete reservoirs 104, and vice versa. "Adjacent" reservoirs may be defined, in some embodiments, as dissimilar reservoirs, which are in physical proximity to each other such that, in the presence of an electrically conductive material between and in contact with the dissimilar reservoirs, an electrical current may be produced between the reservoirs. For example, in a subset 120 of reservoirs shown in FIG. 1, reservoirs 111, 112, 113 and 114 may be considered adjacent to reservoir 116. Other reservoirs beyond subset 120 also may be considered adjacent to reservoir 116, based on the above definition of "adjacent." "Adjacent" reservoirs may be defined, in other embodiments, as a set of selected reservoirs capable of creating, contributing or having electrical communication and/or ionic communication.

Substantially uniform or varying lateral spacings 130 may exist between the perimeters of adjacent reservoirs (e.g., reservoirs 111 and 116). In various embodiments, spacings 130 may be in a range of approximately 0.5 millimeters (mm) to 2.0 mm. In other embodiments, spacings 130 may be larger or smaller than the above range. Lateral spacings 130 may, in various embodiments, be significantly smaller than the above-given values. For example, an apparatus may include very small reservoirs (e.g., "nano-reservoirs"). In such embodiments, lateral spacings 130 may be in a range from approximately 1 nm to approximately 10,000 nm or more. In an embodiment, the physical separation between adjacent dissimilar reservoirs provides for substantial electrical isolation between the adjacent dissimilar reservoirs, absent an electrically conductive material provided between them.

In various embodiments, selected ones of the multiple first discrete reservoirs 102 include a reducing agent, and selected ones of the multiple second discrete reservoirs 104 include an oxidizing agent, or vice versa. In the presence of an electrically conductive material between the first reservoirs and the second reservoirs, redox reactions may be produced between the first and second reservoirs. Although the electrically conductive material may physically contact the reservoirs to facilitate redox reactions, it may be that the redox reactions occur when the conductive material does not physically contact the reservoirs.

Selected ones of the second reservoir surfaces may be positioned in spaced relation to selected ones of the first reservoir surfaces to produce redox reactions between the surfaces, in the presence of an electrically conductive material facilitating electrical and/or ionic communication between the second reservoir surfaces and the first reservoir surfaces. In an embodiment, the redox reactions may occur spontaneously when a conductive material is brought in proximity to first and second dissimilar reservoirs, such that the conductive material provides a medium for electrical communication and/or ionic communication between the first and second dissimilar reservoirs. In other words, in an embodiment, electrical currents may be produced between first and second dissimilar reservoirs without the use of an external battery or other power source (e.g., a direct current (DC) or an alternating current (AC) power source). Accordingly, in various embodiments, an apparatus is provided, which is "electrically self contained," any yet the apparatus may be activated to produce electrical currents. The term "electrically self contained" may be defined, in some embodiments, as being capable of producing electricity without an external battery or power source. In other embodiments, an apparatus may be provided which includes an external battery or power source.

The term "redox reaction" may be defined, in some embodiments, as a reaction involving the transfer of one or more electrons from a reducing agent to an oxidizing agent. The term "reducing agent" may be defined, in some embodiments, as a reactant in a redox reaction, which donates electrons to a reduced species. A "reducing agent" is thereby oxidized in the reaction. The term "oxidizing agent" may be defined, in some embodiments, as a reactant in a redox reaction, which accepts electrons from the oxidized species. An "oxidizing agent" is thereby reduced in the reaction. In various embodiments, a redox reaction produced between a first and second reservoir provides a current between the dissimilar reservoirs.

Figure 2:
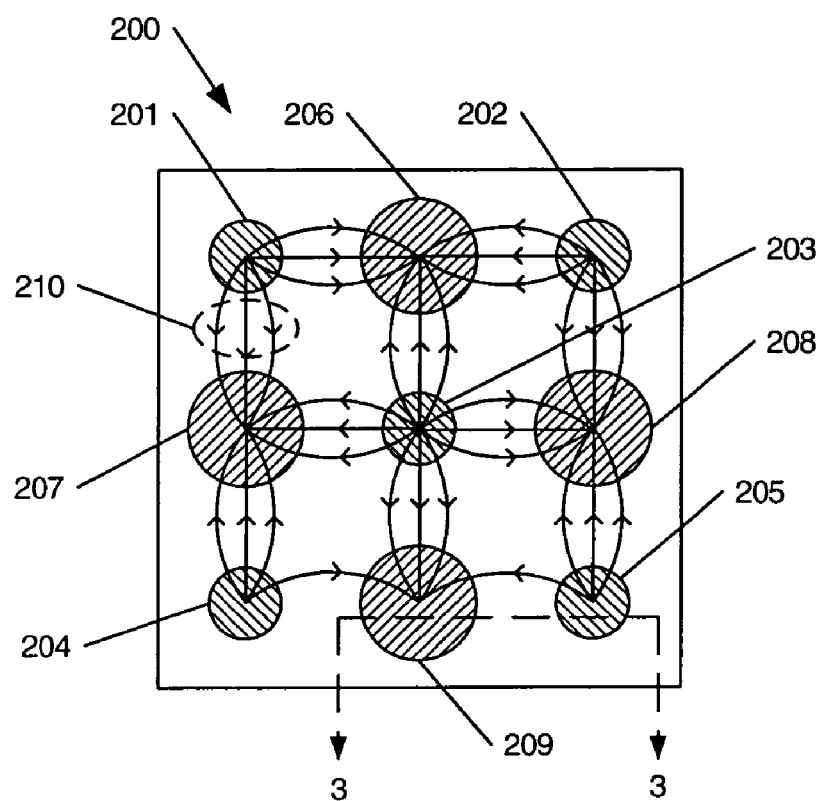
FIG. 2 is a top view of a portion of a medical battery, illustrating current flow between dissimilar reservoirs, in accordance with an example embodiment.

FIG. 2 is a top view of a portion of a medical battery 200, illustrating current flow between dissimilar reservoirs, in accordance with an example embodiment. First reservoirs 201, 202, 203, 204, and 205 may include one or more oxidizing agents, and second reservoirs 206, 207, 208, and 209 may include one or more reducing agents, or vice versa. An electrically conductive material (not illustrated) may be dispersed between some or all of the first reservoirs 201-205 and the second reservoirs 206-209. In the presence of an electrically conductive material between adjacent dissimilar reservoirs, redox reactions may take place, and thus currents may be produced between the adjacent dissimilar reservoirs. Current flows 210 are indicated by arrows between reservoirs 201-205 and reservoirs 206-209. As FIG. 2 illustrates, currents 210 may be produced between each set of adjacent first reservoirs 201-205 and second reservoirs 206-209, in the presence of a conductive material. Accordingly, a field of multiple currents 210 may be produced across a surface of a substrate, creating a planar surface current that includes multiple sub-currents. A current 210 between a set of two adjacent, dissimilar reservoirs may be referred to herein as a "single-cell current," and an aggregate of multiple currents 210 between multiple sets of adjacent, dissimilar reservoirs may be referred to herein as a "multiple-cell current." Currents 210 may be substantially uniform across an active surface, or a varying current density may be present across an active surface.

Each set of adjacent, dissimilar reservoirs (e.g., reservoirs 201 and 206) may form a "galvanic cell," in an embodiment. When a particular reservoir is adjacent to multiple dissimilar reservoirs, then the particular reservoir may form portions of multiple galvanic cells. For example, reservoir 203 may form portions of four or more galvanic cells (e.g., cell A includes reservoirs 203 and 206, cell B includes reservoirs 203 and 207, cell C includes reservoirs 203 and 208, and cell D includes reservoirs 203 and 209).

A "galvanic cell" may be defined, in some embodiments, as an electrochemical cell with a positive cell potential, which may allow chemical energy to be converted into electrical energy. More particularly, a galvanic cell may include a first reservoir serving as an anode and a second, dissimilar reservoir serving as a cathode. Each galvanic cell may store energy in the form of chemical potential energy. When a conductive material is located proximate to a cell such that the material may provide electrical and/or ionic communication between the cell elements, the chemical potential energy may be released as electrical energy. Accordingly, each set of adjacent, dissimilar reservoirs may function as a single-cell battery, and the distribution of multiple sets of adjacent, dissimilar reservoirs within the apparatus may function as a field of single-cell batteries, which in the aggregate forms a multiple-cell battery distributed across a surface.

When a first reservoir includes a reducing agent, and a second reservoir includes an oxidizing agent, or vice versa, a potential difference may exist between the first reservoir and the second reservoir. In a first state, an apparatus is electrically quiescent (e.g., current flow between reservoirs is substantially zero). In an embodiment, an apparatus may be "activated" when a conductive material is brought into proximity with the first reservoir and the second reservoir, enabling a current flow to occur between the reservoirs, via electrical communication and/or ionic communication. Such a conductive material may be referred to herein as an "activation material." A magnitude of the current, I, substantially is a function of the potential difference, V, between the reservoirs, and the conductance or resistance, R, of the conductive material. In other words, the current I between the reservoirs approximately equals the voltage potential, V, between reservoirs divided by the resistance, R, of the conductive material, or $I=V/R$.

Said another way, the magnitudes of currents 210 producible between adjacent, dissimilar reservoirs may be affected by one or more factors, including but not limited to, the distance between adjacent dissimilar reservoirs, the potential difference between the reservoirs (e.g., the quantity of electrons that a reducing agent may have available to donate to an oxidizing agent, the quantity of electrons that an oxidizing agent may be able to accept), resistance of the conductive material, and other factors. In addition, a current between reservoirs may change as a function of time, as the above factors change. Voltage potential differences in a range from approximately 0.05 Volts (V) to approximately 5.0 V may be present between dissimilar reservoirs, in an embodiment. In other embodiments, higher and/or lower voltage differences between dissimilar reservoirs may be present. Further, currents in a range from approximately 1 microampere (mA) to approximately 100 mA may be producible between dissimilar reservoirs, in an embodiment. In other embodiments, higher and/or lower currents may be producible. Resistances of conductive materials may vary significantly from near zero resistance to near infinite resistance.

When an apparatus is applied to an area of tissue and activated (or activated and then applied), a total current, $I_{TOTAL}$, between dissimilar reservoirs may be described as $I_{TISSUE}+I_{(CONDUCTIVE\ MATERIAL)}$. When the resistance of the tissue is greater than the resistance of the conductive material, then proportionally more current may flow through the conductive material than through the tissue. Accordingly, in various embodiments, a conductive material may be selected, which has a resistance that may be greater or less than the anticipated resistance of a type of target tissue, depending on whether more or less current is desired to flow through the target tissue.

In various embodiments, an apparatus may be used to apply electricity to tissue (e.g., skin or other tissue) in need of treatment. The electricity may be generated by a first reservoir (e.g., a first conductive electrode) in electrical communication with a second, dissimilar reservoir (e.g., a second conductive electrode), and the first reservoir and the second reservoir may be in ionic communication with the tissue. The term "electrical communication" may be defined, in some embodiments, as passage of electrons between elements (e.g., first and second reservoirs) through direct contact and/or through a conductive material. The term "ionic communication" may be defined, in some embodiments, as passage of electrons between elements (e.g., first and second reservoirs, a conductive material, and/or tissue) through migration of ions as "electron movers" in contact with the elements (e.g., electrons may pass between a reservoir and tissue via ionic transport of electrolytes in contact with a reservoir and the tissue).

In various embodiments, the difference of the standard potentials of the first and second reservoirs may be in a range from 0.05 V to approximately 5.0 V. In a particular embodiment, the difference of the standard potentials of the first and second reservoirs may be at least 0.2 V. In embodiments that include very small reservoirs (e.g., on the nanometer scale), the difference of the standard potentials may be substantially less. The electrons that pass between the first reservoir and the second reservoir may be generated as a result of the difference of the standard potentials.

Figure 3:
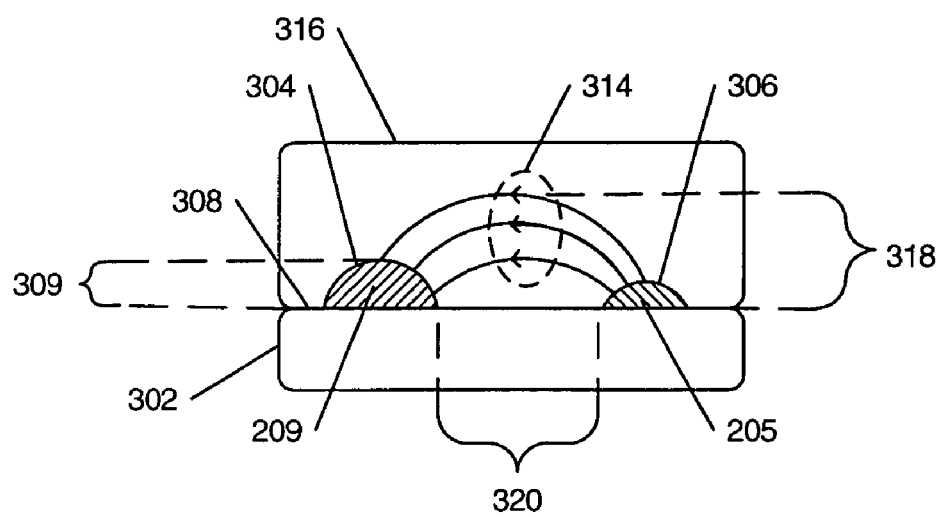
FIG. 3 is a cross-sectional, side view of a portion of the medical battery of FIG. 2 along section line 3-3, in accordance with an example embodiment.

FIG. 3 is a cross-sectional, side view of a portion of the medical battery of FIG. 2 along lines 3-3, in accordance with an example embodiment. The illustrated portion includes a first reservoir 209 and a second reservoir 205 joined with a substrate 302. In the illustrated embodiment, a first reservoir surface 304 and a second reservoir surface 306 extend above a top surface 308 of substrate 302. In other embodiments, either or both reservoir surfaces 304, 306 may be substantially flush with top surface 308 and/or below top surface 308. Further, in the illustrated embodiment, first reservoir surface 304 and second reservoir surface 306 are shown to have a rounded or dome-like shape. In other embodiments, the shape of either or both reservoir surfaces 304, 306 may be substantially flat, disk-like, cylindrical, conical, concave, or otherwise shaped.

In an embodiment, a reservoir may have a height or thickness (e.g., height 309) in a range from approximately 1000 Angstroms to approximately 5 millimeters. In other embodiments, a reservoir may have a height or thickness that is greater than or smaller than the above-given range.

In an embodiment, a current 314 may be produced when a conductive material 316 (e.g., an activation material) is brought into proximity to all or portions of both the first reservoir surface 304 and the second reservoir surface 306, thus enabling electrical communication and/or ionic communication between the surfaces 304, 306. The conductive material 316 may include, but is not limited to, one or more liquid, solid, semi-solid, or gaseous materials, as will be described in more detail later.

In an embodiment, a current 314 may penetrate into the conductive material 316 by a penetration height 318 above the top surface 308 of the substrate. Accordingly, in certain circumstances, current 314 may penetrate into an area of target tissue.

The penetration height 318 of a current may be a function of one or more of various factors, including but not limited to the spacing 320 between reservoir surfaces 304, 306 and other factors. Penetration heights 318 may be substantially uniform across an active surface, or may vary. Currents having penetration heights in a range from approximately 0.05 mm to approximately 2.0 mm are producible, in an embodiment. In other embodiments, currents having higher and/or lower penetration heights may be producible.

In various embodiments, a reservoir may be formed from a single material or a relatively homogenous combination of materials. In other embodiments, a reservoir may be formed from two or more material compositions. Such a reservoir may be referred to herein as a "composite" reservoir.

Figure 4:
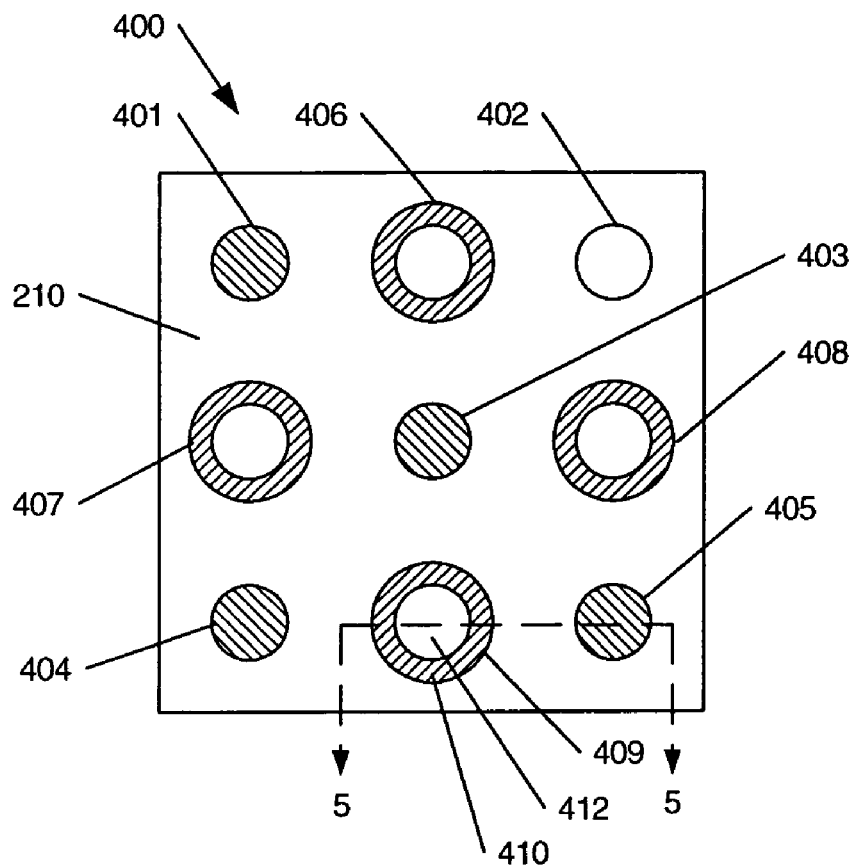
FIG. 4 is a top view of a portion of a medical battery, which includes at least one composite reservoir, in accordance with an example embodiment.

FIG. 4 is a top view of a portion of a medical battery 400, which includes at least one "composite" reservoir, in accordance with an example embodiment. First reservoirs 401, 402, 403, 404, and 405 may function as first portions of galvanic cells, and second reservoirs 406, 407, 408, and 409 may function as second portions of galvanic cells. An electrically conductive material (e.g., an activation material, not illustrated) may be dispersed between some or all of the first reservoirs 401-405 and the second reservoirs 406-409, providing for the production of currents between the first and second reservoirs.

In an embodiment, selected ones of first and/or second reservoirs may be formed from two or more material compositions. For purposes of example, a composite reservoir 409 is shown as being formed from a first composition 410 and a second composition 412. Although certain reservoirs in FIG. 4 are illustrated as being composite reservoirs, it is to be understood that other reservoirs also or alternatively could be composite reservoirs.

First composition 410, in an embodiment, may form a peripheral or outer portion of reservoir 409, and second composition 412 may form an interior or central portion of reservoir 409. In alternative embodiments, a first composition and a second composition may be alternatively arranged, with respect to each other. For example, but not by way of limitation, a first and second composition may be adjacent to each other, layered such that they form a multiple-layer (e.g., two or more), stacked reservoir, or otherwise combined together.

Figure 5:
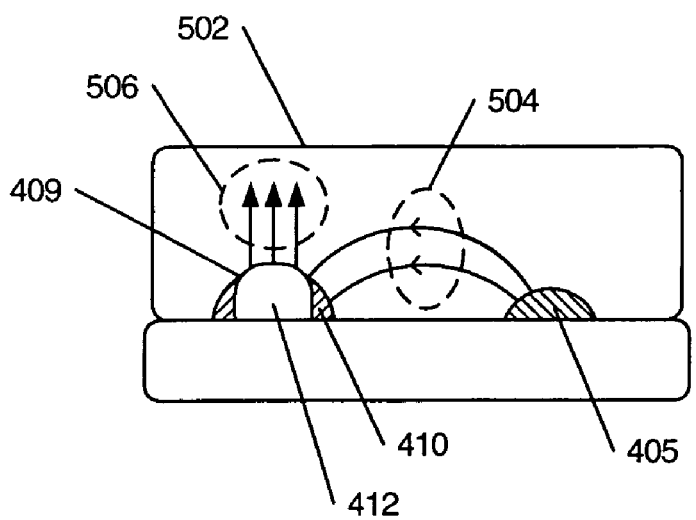
FIG. 5 is a cross-sectional, side view of a portion of the medical battery of FIG. 4 along section line 5-5, in accordance with an example embodiment.

FIG. 5 is a cross-sectional, side view of a portion of the medical battery of FIG. 4 along lines 5-5, in accordance with an example embodiment. In an embodiment, reservoir 409 may function as a first portion of a galvanic cell, and reservoir 405 may form a second portion of the galvanic cell. More particularly, first composition 410 may include a reducing agent, and reservoir 405 may include an oxidizing agent, or vice versa. Accordingly, in the presence of a conductive material 502 between reservoir 405 and first composition 410, a current 504 may be produced between reservoir 405 and first composition 410.

In an embodiment, second composition 412 may include a material which disperses outward (e.g., by iontophoresis, dissolution, or otherwise) from reservoir 409, as indicated by arrows 506. Second composition 412 may, for example, include a material that produces a biological response when it contacts an area of target tissue. In alternative embodiments, first composition 410 and second combination 412 may be oppositely arranged. For example, but not by way of limitation, an inner portion of reservoir 409 may include a reducing (or oxidizing) agent, and an outer portion of reservoir 409 may include a material, which disperses outward from reservoir 409, or vice versa.

As discussed previously, multiple first discrete reservoirs and second, dissimilar discrete reservoirs may be arranged in interleaved patterns, in various embodiments. For example, referring again to FIG. 1, first discrete reservoirs 102 are arranged in rows, and each successive row is offset from the previous row by approximately one-half the distance between the first reservoirs 102. Second discrete reservoirs 104 are interleaved with the first discrete reservoirs 102, and are similarly arranged in rows. In addition, in FIG. 1, selected ones of the first discrete reservoirs 102 may be considered to be adjacent to four or more second discrete reservoirs 104, and vice versa. Accordingly, a correlation of approximately 1:1 may exist between the number of first discrete reservoirs 102 and the number of second discrete reservoirs 104. According to the above-described characteristics of battery 100, interleaved patterns of first and second discrete reservoirs may be defined. In the illustrated embodiment, the patterns are uniformly distributed across the substrate surface. In other embodiments, non-uniform pattern distributions may be present.

In alternative embodiments, a medical battery apparatus may be formed using other configurations of patterns and/or reservoir shapes. FIGS. 6-13 illustrate various alternative embodiments. The illustrated embodiments are not meant to limit the inventive subject matter or the scope of the claims only to the illustrated embodiments. Instead, other configurations of patterns and/or reservoir shapes are contemplated to fall within the scope of the inventive subject matter. In addition, certain cross-hatching is used to differentiate first reservoirs from second, dissimilar reservoirs. It is to be understood that the use of the cross-hatching is not intended to correlate the materials used within those reservoirs to either a reducing agent or an oxidizing agent, as they may have been correlated in the description associated with previously-described figures.

Figure 6:
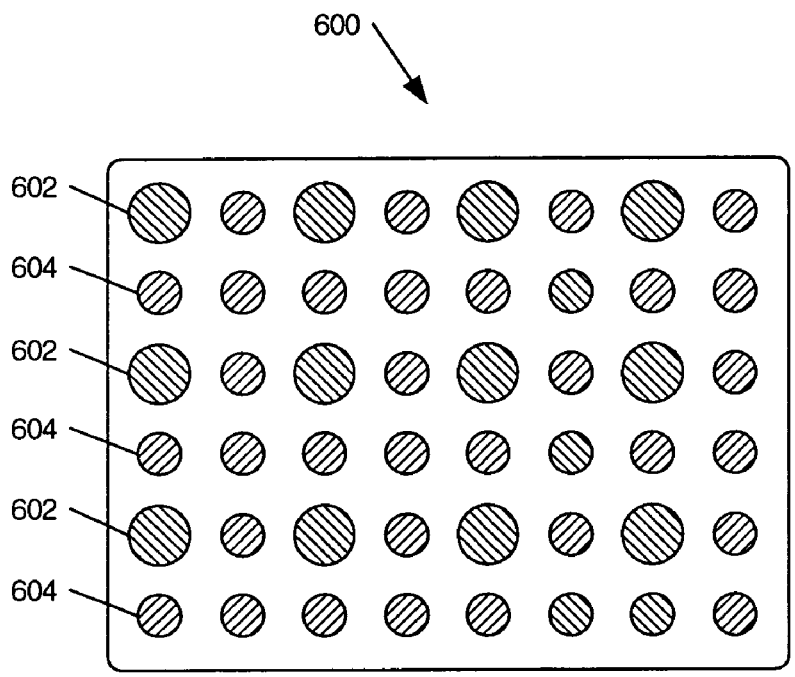
FIG. 6 is a top view of a medical battery having a second configuration of dissimilar reservoirs, in accordance with an example embodiment.

FIG. 6 is a top view of a medical battery 600 having a second configuration of dissimilar reservoirs, in accordance with an example embodiment. Battery 600 includes multiple first reservoirs 602 and multiple second, dissimilar reservoirs 604. In the illustrated embodiment, selected ones of the first discrete reservoirs 602 may be considered to be adjacent to eight or more second discrete reservoirs 604. In addition, selected ones of the second discrete reservoirs 604 may be considered to be adjacent to four or more first discrete reservoirs 602. Accordingly, a number of first discrete reservoirs may be different from a number of second discrete reservoirs (e.g., the correlation between numbers of first and second discrete reservoirs may be substantially different from a 1:1 correlation).

Figure 7:
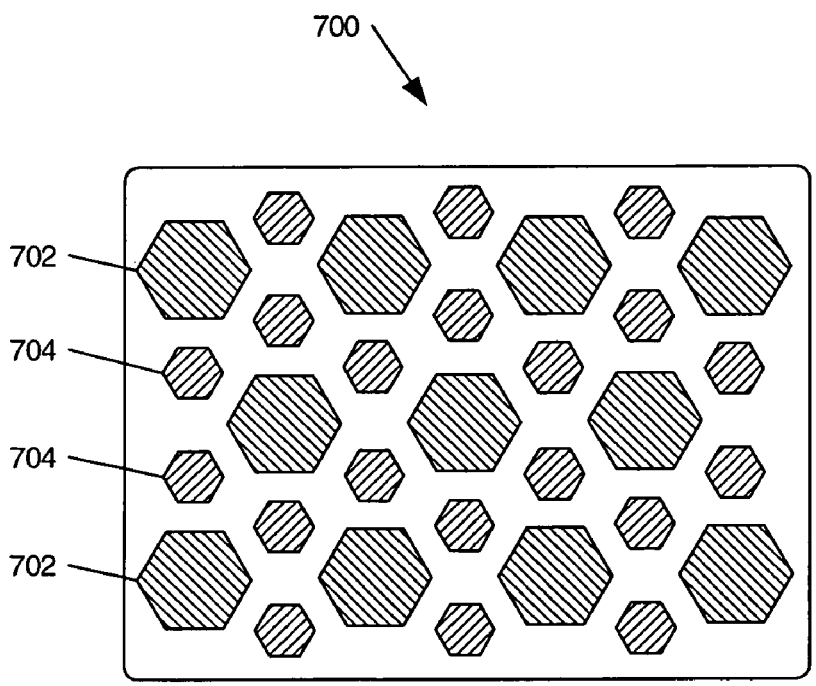
FIG. 7 is a top view of a medical battery having a third configuration of dissimilar reservoirs, in accordance with an example embodiment.

FIG. 7 is a top view of a medical battery 700 having a third configuration of dissimilar reservoirs, in accordance with an example embodiment. Battery 700 includes multiple first reservoirs 702 and multiple second, dissimilar reservoirs 704. In the illustrated embodiment, selected ones of the first discrete reservoirs 702 may be considered to be adjacent to six or more second discrete reservoirs 704. In addition, selected ones of the second discrete reservoirs 704 may be considered to be adjacent to three or more first discrete reservoirs 702.

Figure 8:
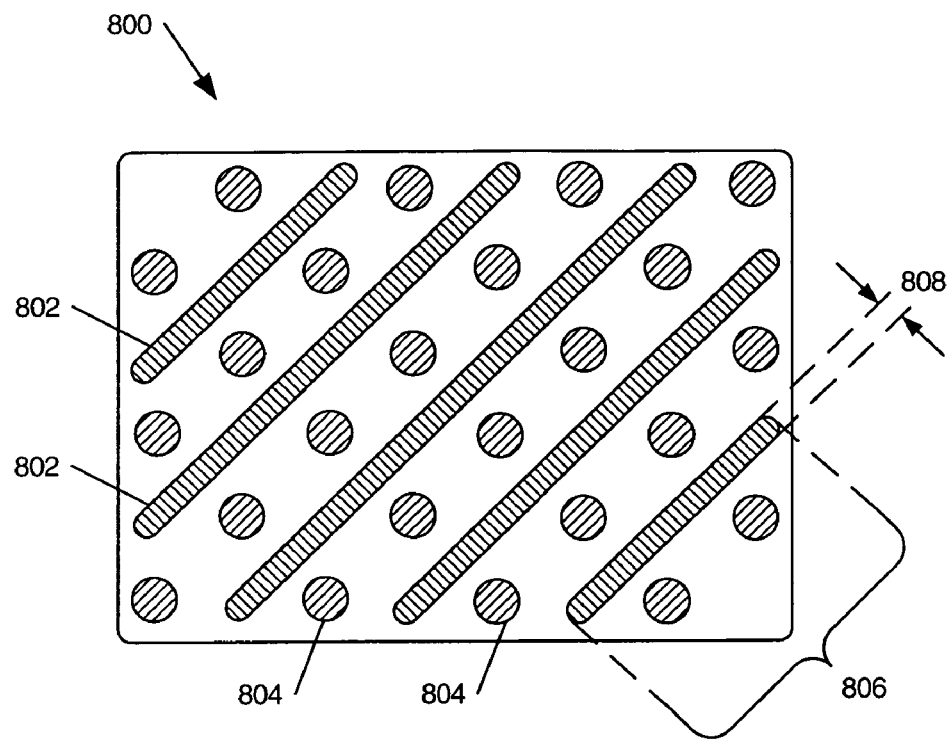
FIG. 8 is a top view of a medical battery having a fourth configuration of dissimilar reservoirs, in accordance with an example embodiment.

FIG. 8 is a top view of a medical battery 800 having a fourth configuration of dissimilar reservoirs, in accordance with an example embodiment. Battery 800 includes multiple first reservoirs 802 and multiple second, dissimilar reservoirs 804. In the illustrated embodiment, selected ones of the first discrete reservoirs 802 are "substantially linear" in shape. The term "substantially linear" may be defined, in some embodiments, as including shapes having a length 806 which is greater than a width 808 by a factor of at least approximately 2:1. A "substantially linear" shape may be substantially straight, or may be curved, coiled or undulating. In the illustrated embodiment, multiple first reservoirs 802 are arranged in a spaced, substantially parallel arrangement to each other, and multiple second discrete reservoirs 804 are arranged in regions between the multiple first reservoirs 802.

Figure 9:
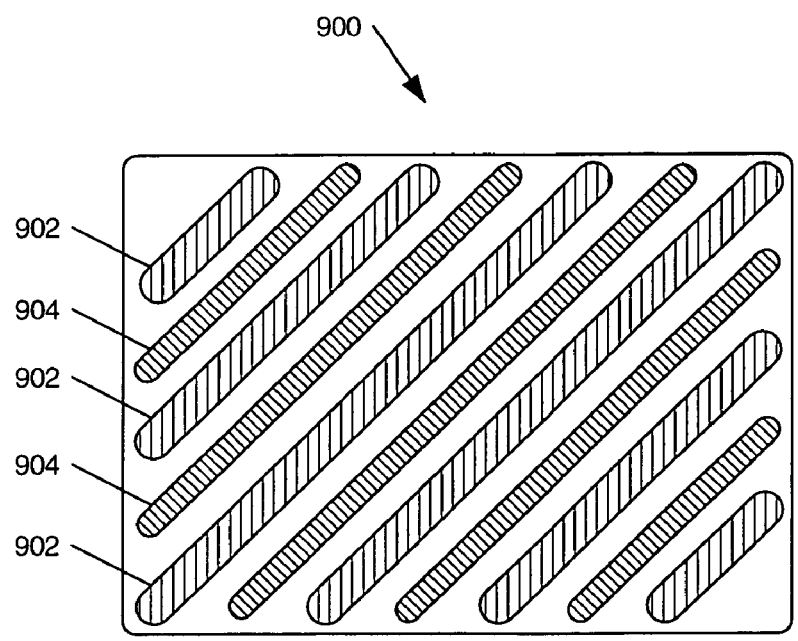
FIG. 9 is a top view of a medical battery having a fifth configuration of dissimilar reservoirs, in accordance with an example embodiment.

FIG. 9 is a top view of a medical battery 900 having a fifth configuration of dissimilar reservoirs, in accordance with an example embodiment. Battery 900 includes multiple first reservoirs 902 and multiple second, dissimilar reservoirs 904. In the illustrated embodiment, selected ones of the first discrete reservoirs 902 and selected ones of the second discrete reservoirs 904 are substantially linear in shape. In the illustrated embodiment, multiple first reservoirs 902 are arranged in a spaced, substantially parallel arrangement to each other, and multiple second discrete reservoirs 904 are arranged in regions between the multiple first reservoirs 902, where the multiple second discrete reservoirs 904 are also arranged in a spaced, substantially parallel arrangement to each other.

Figure 10:
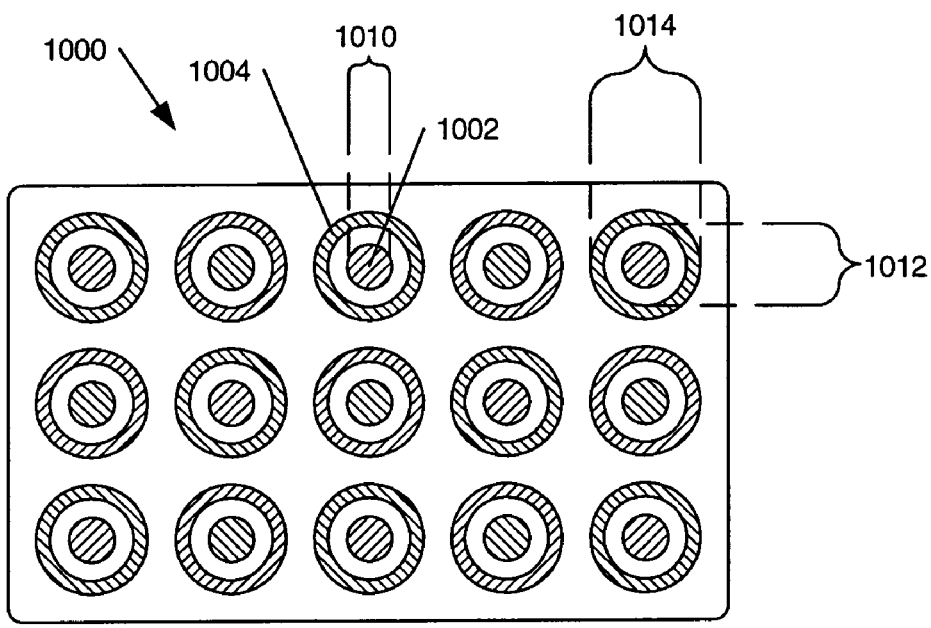
FIG. 10 is a top view of a medical battery having a sixth configuration of dissimilar reservoirs, in accordance with an example embodiment.

FIG. 10 is a top view of a medical battery 1000 having a sixth configuration of dissimilar reservoirs, in accordance with an example embodiment. Battery 1000 includes multiple first reservoirs 1002 and multiple second, dissimilar reservoirs 1004, forming multiple galvanic cells. In the illustrated embodiment, a first discrete reservoir 1002 and a second discrete reservoir 1004 are concentrically arranged, with respect to each other, forming a "concentric" galvanic cell. A first discrete reservoir 1002 is shown as having a circular shape of a first diameter 1010, and a second discrete reservoir 1004 is shown as having a ring shape having an interior diameter 1012 and an exterior diameter 1014. In an embodiment, the interior diameter 1012 of the second discrete reservoir 1004 is larger than the first diameter 1010 of the first discrete reservoir 1002, forming a spacing between the reservoirs. Accordingly, the second discrete reservoir 1004 is concentric with and physically separated from the first discrete reservoir 1002, forming a first galvanic cell. In an embodiment, the materials for adjacent galvanic cells may be reversed, so that additional galvanic cells may be formed from adjacent sets of first and second discrete reservoirs. Alternatively, the materials for adjacent, concentric galvanic cells may be consistently selected.

Figure 11:
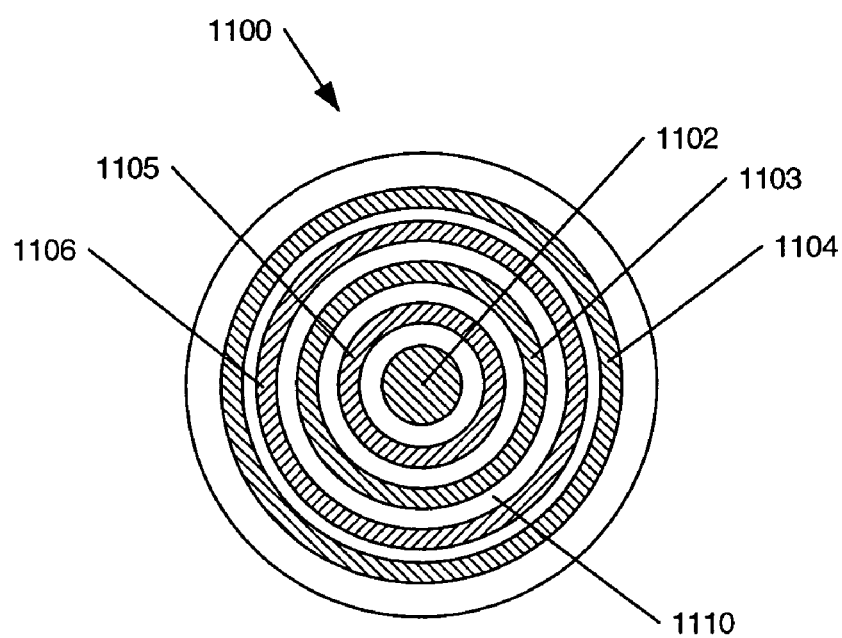
FIG. 11 is a top view of a medical battery having a seventh configuration of dissimilar reservoirs, in accordance with an example embodiment.

FIG. 11 is a top view of a medical battery 1100 having a seventh configuration of dissimilar reservoirs, in accordance with an example embodiment. Battery 1100 includes multiple first reservoirs 1102, 1103, 1104 and multiple second, dissimilar reservoirs 1105, 1106. In the illustrated embodiment, selected ones of reservoirs 1102-1106 may be concentrically arranged, with respect to each other. Spacings 110 may exist between reservoirs 1102-1106 to provide for electrical isolation between adjacent reservoirs, in the absence of a conductive material between the reservoirs.

Embodiments previously described include medical batteries having multiple first reservoirs and multiple second, dissimilar reservoirs. In other embodiments, a medical battery may include a single first reservoir and multiple second, dissimilar reservoirs.

Figure 12:
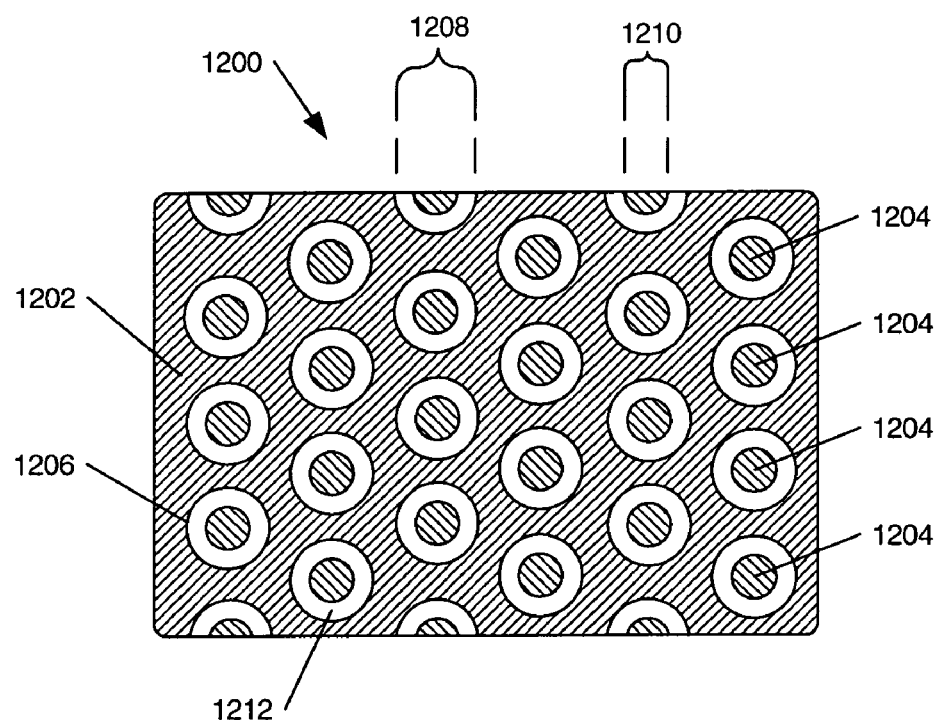
FIG. 12 is a top view of a medical battery having an eighth configuration of dissimilar reservoirs, in accordance with an example embodiment.

FIG. 12 is a top view of a medical battery 1200 having an eighth configuration of dissimilar reservoirs, in accordance with an example embodiment. Battery 1200 includes a single first reservoir 1202 and multiple second, dissimilar reservoirs 1204. In the illustrated embodiment, first discrete reservoir 1202 is "substantially planar," with multiple openings 1206. The term "substantially planar" may be defined, in some embodiments, as including areas of material having a length and a width that are greater than a distance between two or more reservoirs of a first type. A "substantially planar" shape may be substantially flat and uninterrupted, or may have openings, divots, or other interruptions therein. In an embodiment, openings 1206 have a diameter 1208 that is larger than a diameter 1210 of second discrete reservoirs 1204. Accordingly, spacings 1212 exist between the second discrete reservoirs 1204 and the first discrete reservoir 1202.

In still other embodiments, a medical battery may include a single first discrete reservoir and a single second discrete reservoir. For example, but not by way of limitation, first and second discrete reservoirs may be coiled around each other, arranged in a tongue-in-groove, toothed or zig-zag configuration, or otherwise arranged to produce multiple currents across a surface, when a conductive material (e.g., an activation material) is provided between the first and second reservoirs.

In FIGS. 1-12, first discrete reservoirs are shown to be physically separated from second dissimilar reservoirs, thus achieving electrical isolation between the first and second reservoirs, in the absence of a conductive material between the reservoirs. In alternative embodiments, some or all of the dissimilar reservoirs may include areas or points of contact.

Figure 13:
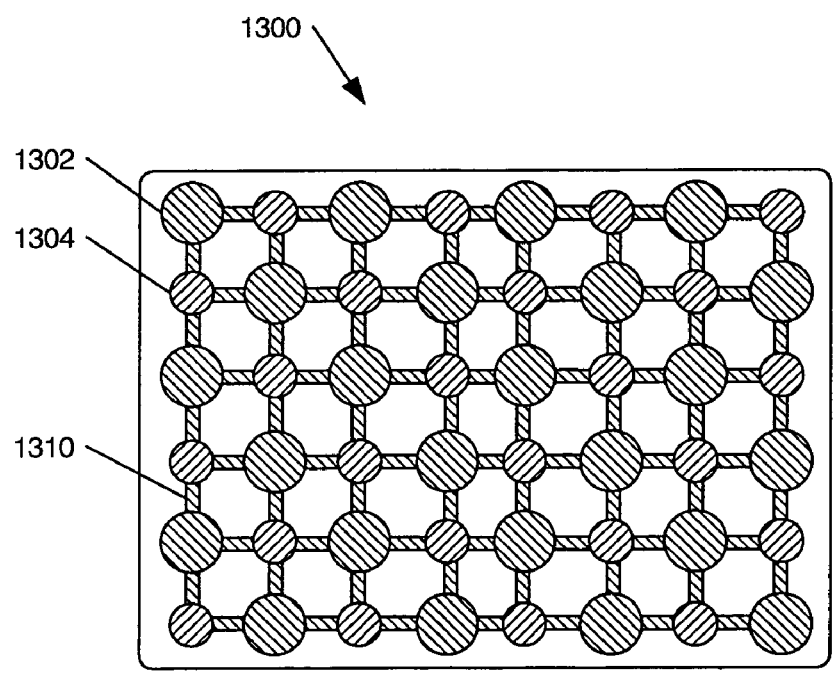
FIG. 13 is a top view of a medical battery having an ninth configuration of dissimilar reservoirs, in accordance with an example embodiment.

FIG. 13 is a top view of a medical battery 1300 having a ninth configuration of dissimilar reservoirs, in accordance with an example embodiment. Battery 1300 includes multiple first reservoirs 1302 and multiple second, dissimilar reservoirs 1304. In addition, battery 1300 includes connecting portions 1310, which may interconnect selected ones or substantially all of the first reservoirs 1302 and the second reservoirs 1304.

In conjunction with FIGS. 14-24, various embodiments for manufacturing a medical battery will now be described, including but not limited to medical battery embodiments previously described. In conjunction with these figures, some materials that may be used to form discrete reservoirs and substrates may be described in accordance with various embodiments. In addition, materials associated with conductive materials (e.g., activation materials) and other apparatus layers or elements may be described in accordance with various embodiments. It is to be understood that the inventive subject matter is not intended to be limited to the various materials described below. In alternative embodiments, various other materials may be used.

Figure 14:
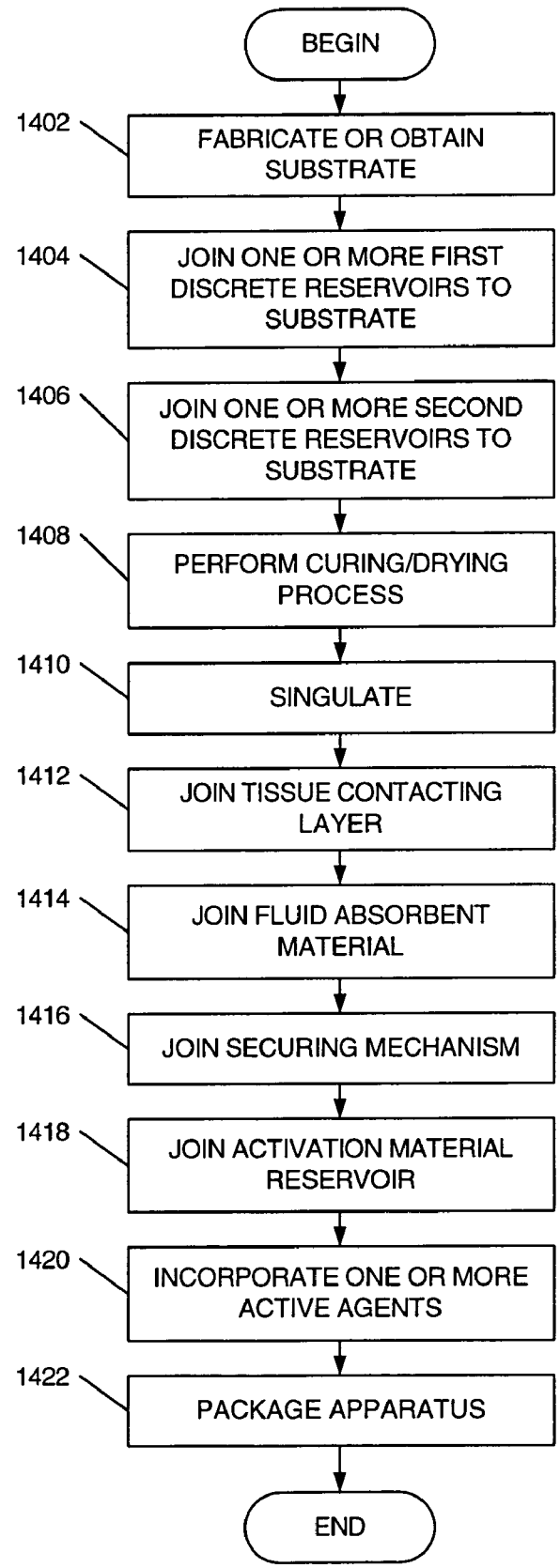
FIG. 14 is a flowchart of a method for manufacturing a medical battery, in accordance with an example embodiment.

FIG. 14 is a flowchart of a method for manufacturing a medical battery, in accordance with an example embodiment. It is to be understood that the processes described in conjunction with the flowchart may be performed in the illustrated order, or may be performed in alternative orders, while achieving substantially the same result. In addition, although the processes are illustrated as occurring consecutively. Some of the processes may be performed concurrently. Furthermore, some of the processes depicted in FIG. 14 may be optionally performed.

In an embodiment, a method includes fabricating or obtaining a substrate having a first surface, in block 1402. A substrate may be formed from a bulk material and/or may include one or more similar or different material layers, sheets or films, in various embodiments.

A substrate may be fabricated into various shapes and sizes corresponding to a variety of target tissue types. A substrate may have a size and shape that may be useful in application to multiple anatomical areas or may have a size and shape that may be useful in application to specific target anatomical areas. In various embodiments, a substrate may be substantially two-dimensional (e.g., having relatively substantial dimensions in two orthogonal directions) or substantially three-dimensional (e.g., having relatively substantial dimensions in three orthogonal directions).

In various embodiments, a substrate may be fabricated to have a first surface (e.g., an active surface) that is flexible (e.g., capable of being contoured or molded to various internal or external anatomical surfaces). In other embodiments, a substrate may be fabricated from one or more substantially non-flexible (e.g., completely or partially rigid or non-conforming) materials.

In various embodiments, the first surface of a substrate, or an apparatus that includes the substrate, may be applied to a target tissue area. Various surfaces to which a substrate or substrate-including apparatus may be applied to, include but are not limited to, healthy or compromised interior or exterior surfaces of skin, eyes, ears, mucous membranes (e.g., oral, buccal, nasal, vaginal, urinary, rectal, and other membranes), gastrointestinal tissue (e.g., esophagus, stomach, intestines), vascular tissue (e.g., heart, arteries, veins), pulmonary tissue (e.g., trachea, lungs, diaphragm), neurological tissue (e.g., brain, spinal cord, cerebrospinal fluid), various internal organs, bone, and cartilage.

In various embodiments, a substrate may include one or more soluble or insoluble materials. The term "insoluble material" may be defined, in some embodiments, as a material which, upon immersion in an aqueous medium, does not readily dissolve or break apart (although it may, given sufficient time). The term "soluble material" may be defined, in some embodiments, as a material which, upon immersion in an aqueous medium, readily or slowly dissolves or breaks apart. For example, but not by way of limitation, a substrate may include one or more biodegradable and/or bioabsorbable materials. The term "bioabsorbable material" may be defined, in some embodiments, as a material which, when absorbed into the body, normally does not provoke a significant toxic or inflammatory response. In various embodiments, a suitable bio-absorbable substrate material may include one or more glasses (e.g., sugar glass or salt glass), bioceramics, natural biodegradable polymers, synthetic biodegradable polymers, other bio-absorbable materials, other soluble materials, or combinations of the like.

When a bioceramic is selected, the material may include one or more materials including alumina, zirconia, calcium phosphate, silica-based glasses, glass ceramics, and pyrolytic carbons. For example, but not by way of limitation, one or more calcium phosphates may be selected from a group of calcium phosphates that includes tetracalcium phosphate, amorphous calcium phosphate, alpha-tricalcium phosphate, beta-tricalcium phosphate, and hydroxyapatite.

When a synthetic biodegradable polymer is selected, the material may include one or more homopolymers or a set of copolymers. Accordingly, a synthetic biodegradable polymer may include one or more polymers (or copolymers) selected from a group of materials that includes esters, polyesters (e.g., polyglycolide (PGA), polylactide (PLA), poly($\epsilon$-caprolactone), poly(lactide-co-glycolide)), polyether-esters, caprolactone (e.g., $\epsilon$-caprolactone), anhydrides, orthoesters, amides, polydioxanone, glycolide, lactide, trimethylene carbonate, polyhydroxybutyrate (PHB), polyhydroxyvalerate (PHV), poly(amino acids), polyesteramides, other synthetic biodegradable polymers, or combinations of the like.

In an embodiment, multiple apparatus may be arranged in a stacked or layered configuration, where one or more of the multiple apparatus include a soluble (e.g., biodegradable and/or bioabsorbable) material. In an embodiment, an outermost apparatus layer may include a first set of one or more dissimilar reservoirs joined to a soluble substrate. Gradually, the soluble substrate and/or the dissimilar reservoirs may degrade, to expose a lower apparatus layer. The lower apparatus layer may include a second set of one or more dissimilar reservoirs joined to a second substrate. The second substrate may be soluble or insoluble. The second set of dissimilar reservoirs may have a similar density and/or configuration, or a different density and/or configuration from the first set of reservoirs. If the second substrate is soluble, the second substrate and/or the second dissimilar reservoirs may gradually degrade, to expose yet another lower apparatus layer, and so on.

In various embodiments, a substrate may include, for example but not by way of limitation, one or more woven materials, non-woven materials, nets, meshes, hydro-entangled materials, and/or air entangled substrates. Further, in various embodiments, a substrate may include one or more fibrous or non-fibrous natural materials and/or synthetic materials. The term "natural material" may be defined, in some embodiments, as materials that are derived from plants, animals, insects, or byproducts of plants, animals, and insects. The term "synthetic material" may be defined, in some embodiments, as materials obtained primarily from various man-made materials or from natural materials, which have been altered.

In various embodiments, a substrate may include one or more materials which include, but are not limited to, poly-tetra-fluoroethylene (PTFE) (e.g., Teflon®), silicone, foams (e.g., polyurethane and/or polymer foams), hydrogels and/or other gels, elastomeric materials, synthetic sponges, natural sponges, silks, keratins (e.g., wool and/or camel hair), cellulosic fibers (e.g., wood pulp fibers, cotton fibers, hemp fibers, jute fibers, and/or flax fibers), rayon, acetates, acrylics, cellulose esters, modacrylics, polymers, super-absorbent polymers (e.g., polymers capable of absorbing approximately 10 times their weight or greater), polyamides, polyesters, polyolefins, polyvinyl alcohols, and/or other materials. In alternative embodiments, a substrate may include one or more additional or different materials from those listed above.

In various embodiments, one or more binding materials may be incorporated into a substrate or onto a surface of a substrate. Binding materials may include, for example but not by way of limitation, one or more of wet strength resins, polymer binder coatings, and/or stable fibers (e.g., cotton, wool, linen, etc.).

In various embodiments, one or more softening additives may be incorporated into a substrate or on a surface of a substrate. Softening additives may include, for example but not by way of limitation, one or more of polyols (e.g., glycerol, propylene glycol, and polyethylene glycol), phthalate derivatives, citric esters, surfactants, and/or acetylated monoglycerides.

Referring back to FIG. 14, in an embodiment, a method for manufacturing a medical battery apparatus includes joining one or more first discrete reservoirs to the substrate, in block 1404. The method also includes joining one or more second discrete reservoirs to the substrate, in block 1406. The processes associated with blocks 1402 and 1404 may be performed sequentially (in forward or reverse order) or simultaneously.

In an embodiment, the one or more first discrete reservoirs and the one or more second discrete reservoirs are joined to the substrate such that selected ones of the first and second reservoirs are physically separated by substrate material. In an embodiment, the substrate material is substantially electrically non-conductive. Accordingly, the physical separations between first and second reservoirs may provide for electrical isolation between the selected reservoirs, in the absence of a conductive material electrically interconnecting the reservoirs. In an alternate embodiment, the substrate material may include electrically conductive characteristics. In another alternate embodiment, one or more connecting elements may be joined to the substrate to interconnect selected ones of the first and second reservoirs.

In an embodiment, a pattern of multiple first discrete reservoirs and a pattern of multiple second discrete reservoirs are joined to the substrate in an interleaved configuration. In other embodiments, a single first discrete reservoir and/or a single second discrete reservoir are joined to the substrate.

The term "join" may be defined, in some embodiments, as including such processes as joining to a surface, adhering to a surface (e.g., using an adhesive), embedding into a hole or depression in a surface, and/or layering onto a surface. Examples of reservoirs joined to a substrate are shown by way of example in FIGS. 15-21. It is to be understood that the illustrated embodiments are for the purposes of example only, and are not meant to limit the scope of the inventive subject matter or the claims only to the illustrated embodiments. For example, it is to be understood that other joining techniques may be used, and/or combinations of joining techniques indicated in the figures may be used, in various embodiments.

Figure 15:
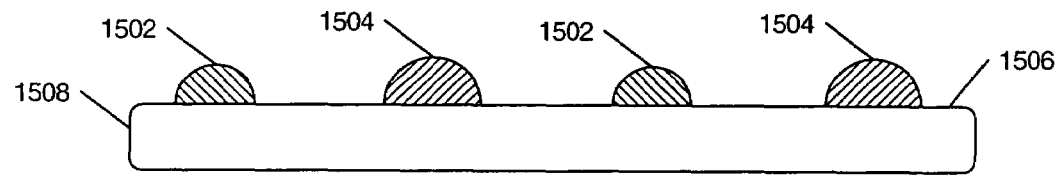
FIG. 15 is a cross-sectional, side view of a portion of a medical battery having multiple first reservoirs and multiple second reservoirs joined to a surface of a substrate, in accordance with an example embodiment.

FIG. 15 is a cross-sectional, side view of a portion of a medical battery having multiple first reservoirs 1502 and multiple second reservoirs 1504 joined to a surface 1506 of a substrate 1508, in accordance with an example embodiment. In various embodiments, first and/or second reservoirs 1502, 1504 may be joined to surface 1506 using any of several techniques. For example, but not by way of limitation, first and/or second reservoirs may be joined to surface 1506 using one or more techniques such as painting or printing (e.g., screen printing or ink jet printing) reservoir material onto surface 1506, depositing reservoir material onto surface 1506 using another deposition process (e.g., chemical deposition, electrochemical deposition, vapor deposition, plating, spray coating, gravure coating, plasma coating, dip coating, nanometer scale deposition, vacuum deposition or sputtering), bonding or fusing reservoir material onto surface 1506.

Figure 16:
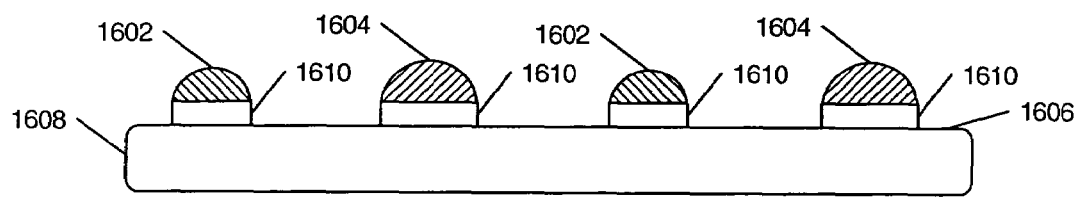
FIG. 16 is a cross-sectional, side view of a portion of a medical battery having multiple first reservoirs and multiple second reservoirs adhered to a surface of a substrate using an adhesive material, in accordance with an example embodiment.

FIG. 16 is a cross-sectional, side view of a portion of a medical battery having multiple first reservoirs 1602 and multiple second reservoirs 1604 adhered to a surface 1606 of a substrate 1608 using an adhesive material 1610, in accordance with an example embodiment. In various embodiments, adhesive material 1610 may be deposited onto surface 1606 prior to or consecutively with adherence of the first and/or second reservoirs 1602, 1604. Adhesive material 1610 may be limited in distribution over the surface 1602, for example as shown in FIG. 16. In an alternative embodiment, adhesive material may be applied as a layer covering a substantial portion of surface 1602.

Figure 17:
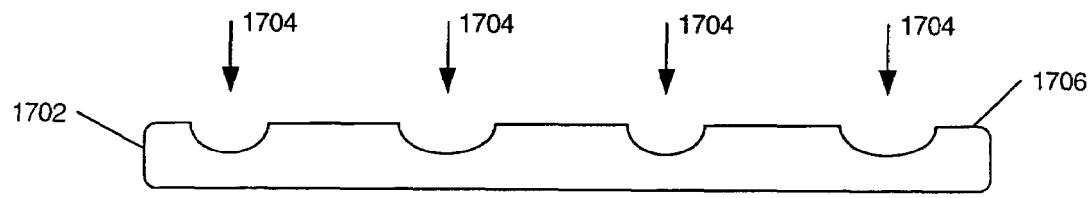
FIG. 17 is a cross-sectional, side view of a portion of a substrate having depressions in a surface, in accordance with an example embodiment.
Figure 18:
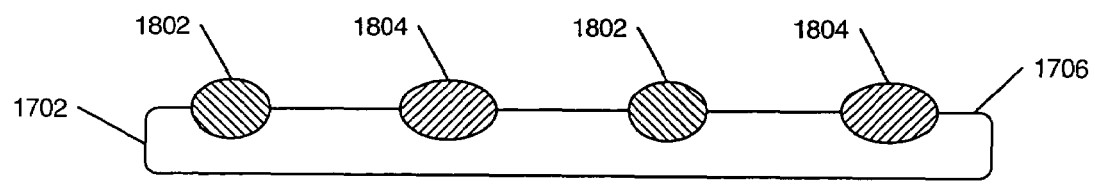
FIG. 18 is a cross-sectional, side view of the substrate of FIG. 17, with multiple first reservoirs and multiple second reservoirs joined to surface within depressions in the substrate, in accordance with an example embodiment.

FIG. 17 is a cross-sectional, side view of a portion of a substrate 1702 having depressions 1704 in a surface 1706, in accordance with an example embodiment. Depressions 1704 may be formed during manufacture of the substrate 1702 or later, in various embodiments. FIG. 18 is a cross-sectional, side view of the substrate of FIG. 17, with multiple first reservoirs 1802 and multiple second reservoirs 1804 joined to surface 1706 within depressions in the substrate 1702 (e.g., depressions 1704, FIG. 17), in accordance with an example embodiment.

Figure 19:
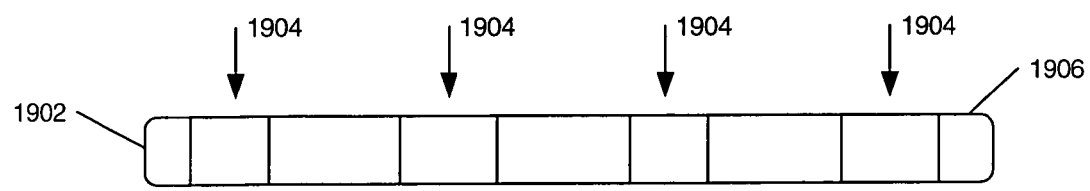
FIG. 19 is a cross-sectional, side view of a portion of a substrate having holes in a surface, in accordance with an example embodiment.
Figure 20:
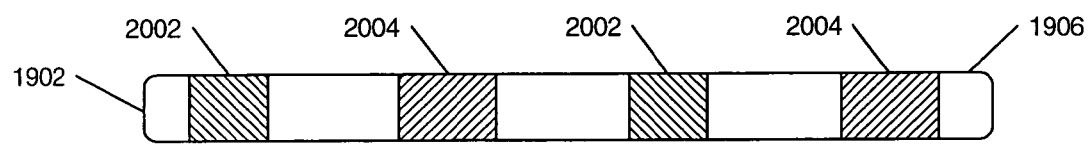
FIG. 20 is a cross-sectional, side view of the substrate of FIG. 19, with multiple first reservoirs and multiple second reservoirs deposited within holes in the substrate, in accordance with an example embodiment.

FIG. 19 is a cross-sectional, side view of a portion of a substrate 1902 having holes 1904 in a surface 1906, in accordance with an example embodiment. Holes 1904 may be formed during manufacture of the substrate 1902 or later, in various embodiments. Although holes 1904 are shown to extend completely through substrate 1902, one or more of the holes may extend only partially through the substrate. FIG. 20 is a cross-sectional, side view of the substrate of FIG. 19, with multiple first reservoirs 2002 and multiple second reservoirs 2004 deposited within holes in the substrate 1902 (e.g., holes 1904, FIG. 19), in accordance with an example embodiment.

Figure 21:
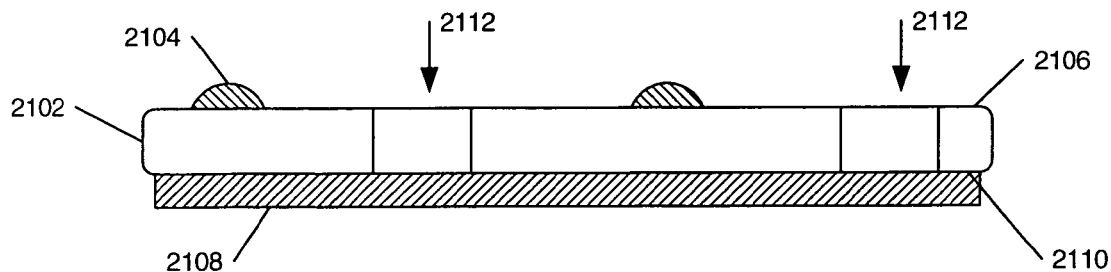
FIG. 21 is a cross-sectional, side view of a portion of a substrate having multiple first reservoirs joined to a first surface of substrate, and a second reservoir provided as a layer joined to a second surface of substrate, in accordance with an example embodiment.

FIG. 21 is a cross-sectional, side view of a portion of a substrate 2102 having multiple first reservoirs 2104 joined to a first surface 2106 of substrate 2102, and a second reservoir 2108 provided as a layer joined to a second surface 2110 of substrate 2102, in accordance with an example embodiment. Holes 2112 may be provided within substrate 2102 to expose portions (e.g., surfaces) of the second reservoir 2104 to the first surface 2106. In an alternate embodiment, both a first reservoir and a second reservoir may form substantially planar reservoir material layers, each of which are selectively exposed to a substrate surface through the inclusion of holes within the substrate. Accordingly, such an apparatus may be characterized as one or more first galvanic reservoirs, joined to a substrate, and having multiple first reservoir surfaces exposed at a first substrate surface, and one or more second galvanic reservoirs, joined to the substrate, and having multiple exposed second reservoir surfaces exposed at the first substrate surface.

Embodiments of apparatus described herein include two or more types of dissimilar reservoirs, where a set of dissimilar reservoirs may form a galvanic cell. In another embodiment, an apparatus may include a first type of reservoir, and when the apparatus is brought into contact with an area of target tissue, the target tissue itself functions as a second, dissimilar reservoir. In such an embodiment, the apparatus' first reservoirs and the target tissue may form one or more galvanic cells.

Various materials may be selected for the first reservoir material and the second reservoir material. The first reservoir material and/or the second reservoir material may substantially include only a single galvanic material, or may include a composite or mixture of multiple galvanic and other materials.

In an embodiment, a first galvanic material included within a first reservoir provides for a first cell of a galvanic couple, and a second galvanic material included within a second reservoir provides a second cell of the galvanic couple. Examples of first galvanic material and second galvanic material combinations may include, but are not limited to, the following:

A) A first galvanic material including, but not limited to, zinc and a second galvanic material including, but not limited to, one or more of: silver, metallic silver, silver oxide, silver chloride, silver bromide, silver iodide, silver fluoride, silver/silver oxide, silver/silver halide, silver/silver chloride, silver/silver bromide, silver/silver iodide, silver/silver fluoride, copper, copper oxide, copper/copper halide, copper/copper oxide, gold, platinum, and conductive carbon;

B) A first galvanic material including, but not limited to, magnesium and a second galvanic material including, but not limited to, one or more of: silver, metallic silver, silver oxide, silver chloride, silver bromide, silver iodide, silver fluoride, silver/silver oxide, silver/silver halide, silver/silver chloride, silver/silver bromide, silver/silver iodide, silver/silver fluoride, copper, copper oxide, copper/copper halide, copper/copper oxide, gold, platinum, and conductive carbon;

C) A first galvanic material including, but not limited to, aluminum and a second galvanic material including, but not limited to, one or more of: silver, metallic silver, silver oxide, silver chloride, silver bromide, silver iodide, silver fluoride, silver/silver oxide, silver/silver halide, silver/silver chloride, silver/silver bromide, silver/silver iodide, silver/silver fluoride, copper, copper oxide, copper/copper halide, copper/copper oxide, gold, platinum, and conductive carbon;

D) A first galvanic material including, but not limited to, iron, and a second galvanic material including, but not limited to, one or more of: silver, metallic silver, silver oxide, silver chloride, silver bromide, silver iodide, silver fluoride, silver/silver oxide, silver/silver halide, silver/silver chloride, silver/silver bromide, silver/silver iodide, silver/silver fluoride, copper, copper oxide, copper/copper halide, copper/copper oxide, gold, platinum, and carbon;

E) A first galvanic material including, but not limited to, copper, and a second galvanic material including, but not limited to, one or more of: silver, metallic silver, silver oxide, silver chloride, silver bromide, silver iodide, silver fluoride, silver/silver oxide, silver/silver halide, silver/silver chloride, silver/silver bromide, silver/silver iodide, silver/silver fluoride, and conductive carbon; and F) A first galvanic material including, but not limited to, one or more of: zinc, magnesium, aluminum, iron, calcium, tin, copper, and alloys thereof; and a second galvanic material including, but not limited to, one or more of: silver, metallic silver, silver oxide, silver chloride, silver bromide, silver iodide, silver fluoride, silver/silver oxide, silver/silver halide, silver/silver chloride, silver/silver bromide, silver/silver iodide, silver/silver fluoride, copper, copper oxide, copper/copper halide, copper/copper oxide, gold, platinum, carbon, and conductive carbon;

G) A first galvanic material including, but not limited to, one or more alloys of: zinc, magnesium, aluminum, iron, calcium, tin, copper, and alloys thereof; and a second galvanic material including, but not limited to, one or more of: silver, metallic silver, silver oxide, silver chloride, silver bromide, silver iodide, silver fluoride, silver/silver oxide, silver/silver halide, silver/silver chloride, silver/silver bromide, silver/silver iodide, silver/silver fluoride, copper, copper oxide, copper/copper halide, copper/copper oxide, gold, platinum, carbon, and conductive carbon;

H) A first galvanic material including, but not limited to, one or more of: zinc, magnesium, aluminum, iron, calcium, tin, copper, and alloys thereof; and a second galvanic material including, but not limited to, one or more alloys of: silver, metallic silver, silver oxide, silver chloride, silver bromide, silver iodide, silver fluoride, silver/silver oxide, silver/silver halide, silver/silver chloride, silver/silver bromide, silver/silver iodide, silver/silver fluoride, copper, copper oxide, copper/copper halide, copper/copper oxide, gold, platinum, carbon, and conductive carbon.

In the above lists of materials, the convention a/b may indicate a halide of "a." Accordingly, for example, the term "silver/silver chloride" indicates a silver halide Ag/AgCl. When halides are used in a first reservoir, an electrochemical reaction at the surface of a second reservoir may result in conversion of the halide to a pure metal (e.g., metallic silver) and halide ions. The terms "silver" and "metallic silver" may be used interchangeably herein. Use of the term "silver" includes "metallic silver."

The scope of the claimed subject matter is not meant to be limited to the above-listed galvanic material combinations. Further, a particular galvanic material may include multiple of the above-listed and/or other materials. In other embodiments, other materials may be selected for either or both a first galvanic material or a second galvanic material. For example, but not by way of limitation, one or more galvanic materials may include a polymer or an organic material.

The first reservoir and/or the second reservoir may include the first galvanic material and the second galvanic material in the form of a solid bulk material, sheets, foils, crystals, flakes, wires, slugs, pucks, disks, granules, needles, dust, powder, tubes, meshes, wools, rods, and/or shots, in various embodiments. For example, but not by way of limitation, in an embodiment, a first galvanic reservoir material may include silver crystals. In an embodiment, silver crystals may have sizes smaller than approximately 100 microns, although crystals having larger sizes may alternatively be used. In another embodiment, silver crystals may have average sizes of approximately 40 microns, although crystals having larger or smaller average sizes may alternatively be used. In an embodiment, a second galvanic reservoir material may include zinc crystals. In an embodiment, zinc crystals may have sizes smaller than approximately 100 microns, in an embodiment, although crystals having larger sizes may alternatively be used. In another embodiment, zinc crystals may have average sizes of approximately 40 microns, although crystals having larger or smaller average sizes may alternatively be used.

According to various embodiments, the first and/or second reservoirs may be "reactive reservoirs" or "inert reservoirs." The term "inert reservoir" may be defined, in some embodiments, as a reservoir that may not undergo a significant change in its chemical composition during a redox reaction. In an embodiment, a reservoir may include or be coated with an inert material, so that an electrochemical process at the surface of the reservoir may generate oxidizing agents (e.g., nascent oxygen) and/or chlorine-containing oxidizing agents.

The term "reactive reservoir" may be defined, in some embodiments, as a reservoir that may undergo changes in its chemical composition during a redox reaction, which changes may occur when the apparatus is activated. In an embodiment, a reactive reservoir may include one or more reactive materials, which include but are not limited to, zinc, aluminum, copper, magnesium, manganese, silver, titanium, tin, iron, and alloys thereof. Upon passage of an electric current through a reactive reservoir, ions such as zinc, copper, magnesium, manganese, and/or aluminum cations may be released from the reservoir into a conductive material and/or into an area of target tissue. Such ions may or may not have therapeutic benefits, which may include, but are not limited to, anti-microbial effects, immunologic modulation, enzymatic regulation, cellular induction, modulation of cellular differentiation and/or de-differentiation, modulation of cellular apoptosis, modulation of cellular morphology, modulation of cellular function, modulation of cellular activity, modulation of cellular chemical activity and/or behavior, and/or anti-inflammatory effects.

In various embodiments, one or more additional materials may be included with the galvanic materials in the first reservoir material and/or the second reservoir material. In an embodiment, a galvanic material may be mixed with the one or more additional materials to form a reservoir material prior to joining the material with the substrate.

For example, but not by way of limitation, one or more soluble and/or insoluble binders may be included within a first reservoir material and/or a second reservoir material. A "binder" may be defined, in some embodiments, as a material that attaches other materials within a reservoir to a substrate. A binder may include, for example but not by way of limitation, a biocompatible liquid, a polymeric binder, a polyethylene binder, an acrylic binder, an ink (e.g., a polyacrylic ink), and/or other materials. In other embodiments, a first reservoir material and/or a second reservoir material may not include a binder.

In an embodiment, a binder material may include a material that degrades (e.g., biodegrades, dissipates, or otherwise breaks down) in the presence of an activation material. As a binder material degrades, more galvanic material may be exposed to a reservoir surface. Eventually, substantially all material within a reservoir may degrade.

A type of binder selected and a ratio of binder material to galvanic material, within a reservoir, may be selected to affect a rate at which galvanic material and/or other materials are released from a reservoir (e.g., a rate at which a reservoir degrades). In an embodiment, a range of galvanic material percentages, by weight, within a reservoir material may be approximately 10% galvanic material to approximately 40% galvanic material. In another embodiment, a range of galvanic material percentages within a reservoir material may be approximately 5% galvanic material to approximately 10% galvanic material. In another embodiment, a range of galvanic material percentages within a reservoir material may be approximately 40% galvanic material to approximately 100% galvanic material. In other embodiments, different galvanic material percentage ranges may be included in a reservoir material.

The materials selected for the first and/or second reservoirs may be in a first state at the time they are joined to a substrate, and further processing steps may be performed to transform the materials to a second state. For example, various forming, curing, drying, and/or other processing procedures may be performed.

Referring again to FIG. 14, the apparatus may optionally be subjected to one or more curing and/or drying ("curing/drying") processes, in block 1408. Although a curing/drying process is illustrated to occur after joining one or more second discrete reservoirs to the substrate (block 1406), it is to be understood that a curing/drying process also may be performed prior to joining the one or more second reservoirs. In an embodiment, a curing/drying process may be performed after both blocks 1404 and 1406.

A curing or drying process may include exposing the apparatus to a heat source and/or light source for one or multiple time periods. Curing and/or drying may affect the characteristics of a first reservoir and/or a second reservoir. For example, a reservoir surface may be substantially smooth prior to curing or drying. Upon the performance of one or more curing or drying processes, surface discontinuities (e.g., cracks, holes, etc.) may be introduced. Such discontinuities may function to increase the effective surface area of a reservoir. Accordingly, rates of iontophoresis, reservoir material release, reservoir dissolution, and/or other processes may be affected.

Figure 22:
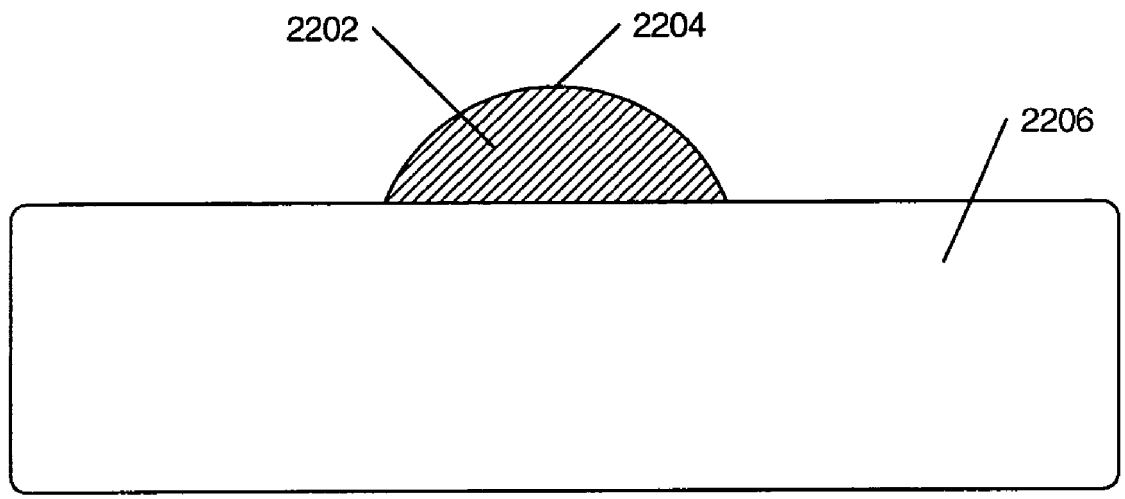
FIG. 22 illustrates a reservoir having a substantially smooth reservoir surface, joined with a substrate, in accordance with an example embodiment.
Figure 23:
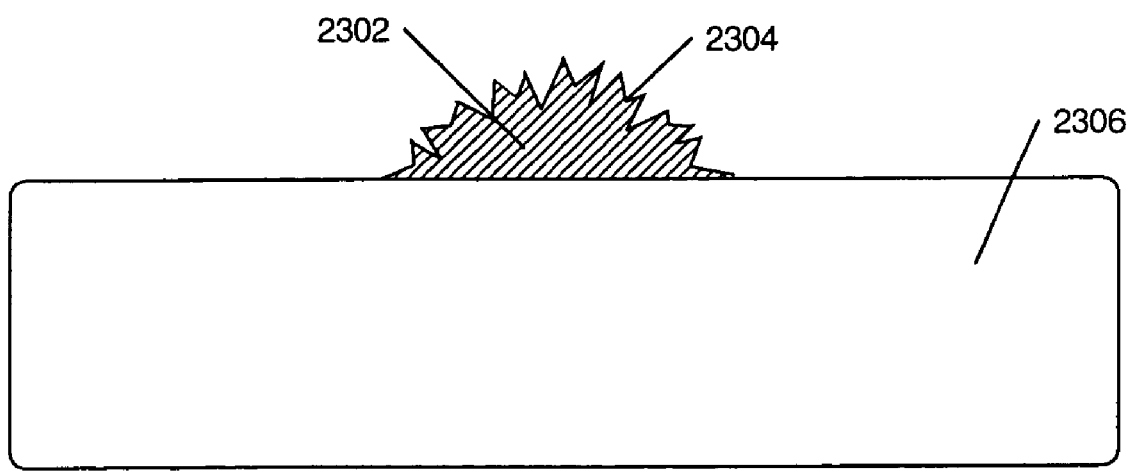
FIG. 23 illustrates a reservoir having a reservoir surface with significant surface discontinuities, in accordance with an example embodiment.

FIG. 22 illustrates a reservoir 2202 having a substantially smooth reservoir surface 2204, joined with a substrate 2206, in accordance with an example embodiment. Conversely, FIG. 23 illustrates a reservoir 2302 having a reservoir surface 2304 with significant surface discontinuities, in accordance with an example embodiment. Reservoir 2302 provides an example of the effects that a curing or drying process may have on the characteristics of a reservoir surface.

Referring again to FIG. 14, in block 1410, a singulation process may optionally be performed to produce multiple medical batteries from the substrate. Singulation may include cutting, sawing, tearing, or otherwise separating a substrate into multiple pieces. In another embodiment, one or more lines of perforation or indentation may be imprinted into a substrate surface, to enable an end-user easily to singulate a medical battery during future use.

In block 1412, a tissue contacting layer may optionally be joined to an active surface of the substrate. In an embodiment a tissue contacting layer may include a cover layer. In an embodiment, a cover layer may include a material that may absorb activation materials (e.g., a conductive material). Alternatively, a cover layer may include, for example but not by way of limitation, a material that is non-absorbent. A cover layer may be soluble or non-soluble, and/or electrically conductive or non-conductive, in various embodiments. For example, but not by way of limitation, a cover layer may include a polymer, polyethylene, polypropylene, polyvinyl acetate, polyurethane), silicone rubber, and/or polyvinyl chloride. In alternate embodiments, a cover layer may include one or more other types of material. In an embodiment, a cover layer is selected such that materials (e.g., silver, zinc, and/or other materials) within a first reservoir and/or a second reservoir may readily penetrate through the cover layer and onto or into the area of target tissue.

In block 1414, a fluid absorbent material may optionally be joined to a top surface and/or a bottom surface of the apparatus. For example, but not by way of limitation, a fluid absorbing material may include one or more polymers, polymers prepared by monomers, gelatin, gums and polysaccharides, polyethylene glycol, polypropylene glycol, clays, swellable minerals, and/or other fluid absorbent materials.

In block 1416, a securing mechanism may optionally be joined to the apparatus. For example, in an embodiment, a securing mechanism may include a flexible sheet (e.g., formed from a material such as a polymer) and an adhesive layer. In an embodiment, the adhesive layer may be covered by a removable liner sheet, to protect the adhesive from compromise prior to use.

In block 1418, an activation material reservoir and/or an activation material may optionally be joined to or provided with the apparatus. In an embodiment, an activation material includes a conductive material. A conductive material may include, for example, a liquid (e.g., a solution, suspension, or emulsion), a semi-solid (e.g., a gel, ream lotion, microemulsion or hydrogel), a solid, or a gaseous material. An activation material reservoir may include, for example, an apparatus, which may be selectively opened or broken to release or expose a conductive material to the reservoirs and/or target tissue. The material may flow onto or into the apparatus and/or onto an area of target tissue. Alternatively, the activation material may be placed by a user onto the apparatus or onto an area of target tissue.

As described previously, when a conductive material is brought in proximity to a galvanic cell, a redox reaction may occur between the cell components (e.g., a first reservoir and a second reservoir). In various embodiments, conductive materials included in a conductive material reservoir may include, but are not limited to, one or more of water, saline, organic or inorganic salts or buffers, electrolyte-active agents, hydrogel, and/or organic solvents. In other embodiments, redox reactions may occur when a galvanic cell is brought in proximity to another liquid material, a solid material, a semi-solid material, a gaseous material, wound exudation fluid and/or other biologically-produced fluids or conductive materials. Accordingly, these materials also may be considered to be activation materials. The term "biologic activation materials" may be defined, in some embodiments, as activation materials that are produced by a biologic entity.

An activation material may also include one or more additional materials, such as for example but not by way of limitation, one or more active agents, preservatives, stabilizing agents or antioxidants, chelating agents, buffers, tonicity adjusting agents, suspending materials, and/or fluid-absorbing materials.

Figure 24:
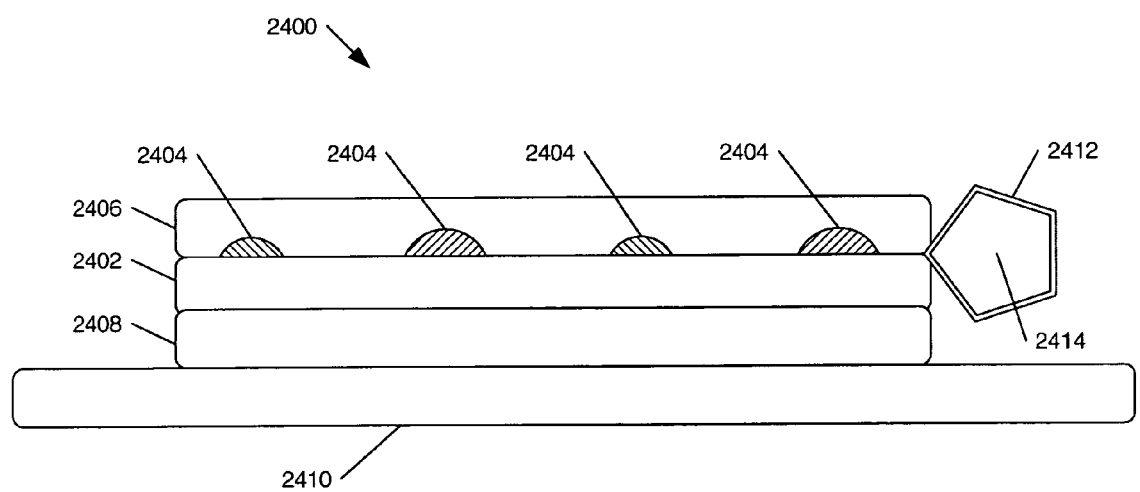
FIG. 24 illustrates a cross-sectional, side view of an apparatus having a substrate, reservoirs, a tissue contacting layer, a fluid absorbing layer, a securing mechanism, an activation material reservoir, and an activation material, in accordance with an example embodiment.

FIG. 24 illustrates a cross-sectional, side view of an apparatus 2400 having a substrate 2402, reservoirs 2404, a tissue contacting layer 2406, a fluid absorbing layer 2408, a securing mechanism 2410, an activation material reservoir 2412, and an activation material 2414, in accordance with an example embodiment. It is to be understood that various combinations of the tissue contacting layer 2406, fluid absorbing layer 2408, securing mechanism 2410, activation material reservoir 2412, activation material 2414, and liner sheet 2416 may be included in apparatus according to other embodiments. Further, in various embodiments, none of components 2406, 2408, 2410, 2412, 2414, and 2416 may be included in an apparatus. Further, in various embodiments, some or all of the components illustrated in FIG. 24 (including substrate 2402 and reservoirs 2404) may have different quantities, shapes, relative sizes, or relative positions with respect to each other than the shapes, sizes, and relative positions illustrated in FIG. 24. The quantities, shapes, relative sizes, and relative positions of the components illustrated in FIG. 24 are to provide a conceptual example, and are not meant for limitation purposes.

Referring back to FIG. 14, in block 1420, one or more active agents may optionally be incorporated into or onto an apparatus element, such as a substrate, one or more reservoirs, an activation material, or another apparatus component. In various embodiments, an active agent may be incorporated in the form of dissolved molecules and/or ions, dispersed solid particles, and/or liquid droplets (e.g., creams, lotions, emulsions, and/or liposome compositions). An "active agent" may include a synthetic compound or a compound isolated from a natural source, which has an effect on biologic tissue, including but not limited to, a cosmetic effect, a therapeutic effect, a chemical effect, a morphologic effect, and/or a cellular effect, including but not limited to, cellular induction, modulation of cellular differentiation and/or de-differentiation, modulation of cellular apoptosis, modulation of cellular morphology, modulation of cellular function, modulation of cellular activity, modulation of cellular chemical activity and/or behavior. In various embodiments, an amount of active agent incorporated into or onto an apparatus element may be a "safe and effective amount" (e.g., from approximately 0.001% to about 20%, by weight, of the element into or onto which the active agent is incorporated).

Active agents may include, for example but not by way of limitation, one or more of a therapeutic drug (e.g., peptides, polypeptides, proteins, nucleic acid materials, hormones, fats, carbohydrates, complex molecules, and/or nutrients), wound-healing enhancing agents (e.g., recombinant human platelet-derived growth factor and/or other growth factors), ketanserin, iloprost, scar-reducing agents, hair growth enhancing agents, hair growth retarding agents, antihypertensives, anticancer agents, endocrine and metabolic medication, neurologic medications, motion sickness reduction agents, protein and peptide drugs, anti-acne agent, anti-rosacea agent, anti-aging agent (e.g., sunscreens, vitamins, vitamin salts, alpha hydroxy acids and their precursors, beta hydroxyl acids, zinc and zinc-containing compounds, botanical extracts, and salts), depigmentation agents, plant extracts, metals, anesthetics, analgesics, drugs for treating psychiatric disorders, epilepsies, and migraine, drugs for stopping drug additions, anti-inflammatory agents, drugs to treat hypertension, cardiovascular diseases, gastric acidity and ulcers, drugs for hormone replacement therapies and contraceptives, antibiotics, antifungal agents, antiviral agents, antipsoriatic agents, other antimicrobial agents, anti-inflammatory agents, antineoplastic agents, immunosuppressive agents, immunostimulants, drugs acting on blood and blood forming organs, vaccines, and/or antivenins.

Referring again to FIG. 14, in block 1422, the apparatus may optionally be packaged. In an embodiment, packaging includes providing a covering over the apparatus, which protects the apparatus from environmental or physical damage, prior to use. The method then ends.

In an embodiment, an apparatus is adapted for use as a conformable, tissue contacting apparatus (e.g., a skin, wound, or mucous membrane tissue contacting device, such as a therapeutic patch, mask, or wound dressing, or other dressing), and may have an active surface area from approximately 1 square centimeter ($cm^2$) to approximately 50 $cm^2$, and a thickness from approximately 1 mm to approximately 10 mm. In another embodiment, an apparatus is adapted for use as an eye contacting apparatus, and may have an active surface area from approximately 1 $cm^2$ to approximately 2 $cm^2$. In another embodiment, an apparatus is adapted for use as an ear canal insert, and may have an active surface area from approximately 1 $cm^2$ to approximately 10 $cm^2$. In another embodiment, an apparatus is adapted for use as an intravaginal apparatus (e.g., a tampon, diaphragm, sponge, pessary), and may have an active surface area from approximately 5 $cm^2$ to approximately 200 $cm^2$. In another embodiment, an apparatus is adapted for use as an internal prosthetic device, and may have an active surface area from approximately 1 $cm^2$ to approximately 100 $cm^2$. In another embodiment, an apparatus is adapted for use as an internal medical device (e.g., a stent, inter-uterine device, intravenous catheter, urinary tract catheter, tracheal tube, feeding tube, screw, clamp), and may have an active surface area from approximately 1 $cm^2$ to approximately 500 $cm^2$. In another embodiment, an apparatus is adapted for use as a medical instrument (e.g., a surgical instrument, mask, diagnostic device, etc.), and may have an active surface area from approximately 1 $cm^2$ to approximately 100 $cm^2$. In another embodiment, an apparatus is adapted for use as a clothing article (e.g., a gown, garment, glove, sock, head covering, etc.), and may have an active surface area from approximately 1 $cm^2$ to approximately 10,000 $cm^2$. In another embodiment, an apparatus is adapted for use as a wipe or towel, and may have an active surface area from approximately 20 $cm^2$ to approximately 10,000 $cm^2$. The above-given dimensional ranges are for the purpose of example, and not of limitation. Accordingly, the above-listed apparatus may have active surfaces and/or thicknesses having larger or smaller dimensions, in alternate embodiments. For example, in applications that include "nano-reservoirs," as discussed previously, various apparatus dimensions may be significantly smaller than the above-given ranges.

Various apparatus are illustrated in FIGS. 25-30, in which embodiments of the inventive subject matter may be included. It is to be understood that the illustrated apparatus are for example purposes, and are not to be construed to limit application of various embodiments only to these apparatus. In contrast, embodiments of the inventive subject matter may be incorporated into a wide variety of other apparatus. Accordingly, incorporation of the inventive subject matter into other apparatus, including but not limited to those listed in the previous paragraph, is intended to fall within the scope of the claims.

Figure 25:
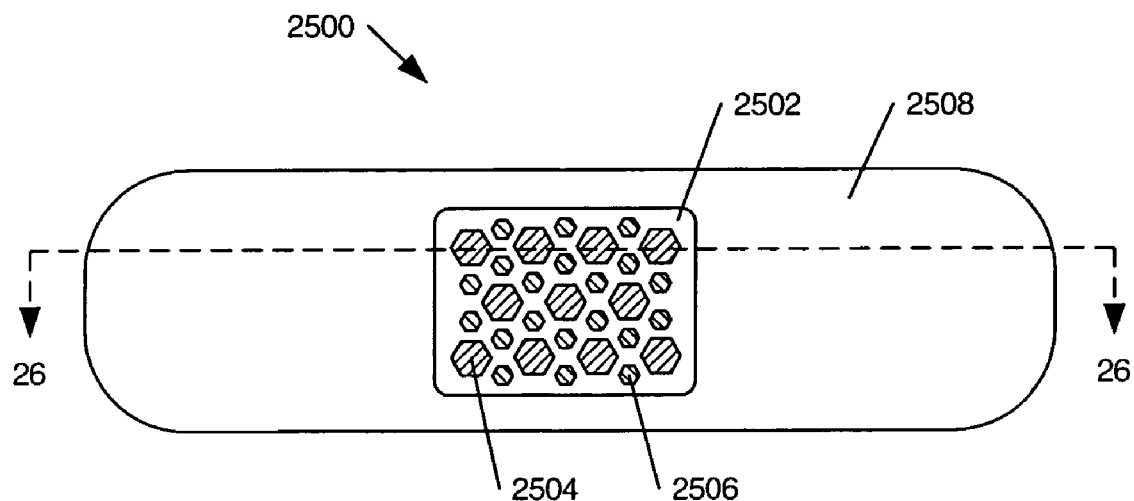
FIG. 25 is a top view of a wound dressing, in accordance with an example embodiment.

FIG. 25 is a top view of a wound dressing 2500, in accordance with an example embodiment. Dressing 2500 may include a substrate 2502, first galvanic reservoirs 2504, second, dissimilar galvanic reservoirs 2506, and a securing mechanism 2508. Multiple first and second galvanic reservoirs 2504, 2506 may be joined with substrate 2502, and substrate 2502 may be joined with securing mechanism 2508. In an embodiment, securing mechanism 2508 includes a material (not illustrated) on its top surface, which may function to hold substrate 2502 in place, with respect to the securing mechanism 2508. Further, the material may extend beyond the boundaries of substrate 2502, and may function to hold wound dressing 2500 in a fixed position with respect to an area of target tissue.

In the illustrated embodiment, the surface area of substrate 2502 corresponds to approximately 25% of the tissue facing surface area of the dressing 2500. In other embodiments, the proportional surface area of substrate 2502 with respect to the total tissue facing surface area of the dressing 2500 may be larger or smaller than 25%. In addition, in various embodiments, the shapes of the substrate 2502, reservoirs 2504, 2506, and/or securing mechanism 2508 may be different from the illustrated shapes.

Figure 26:
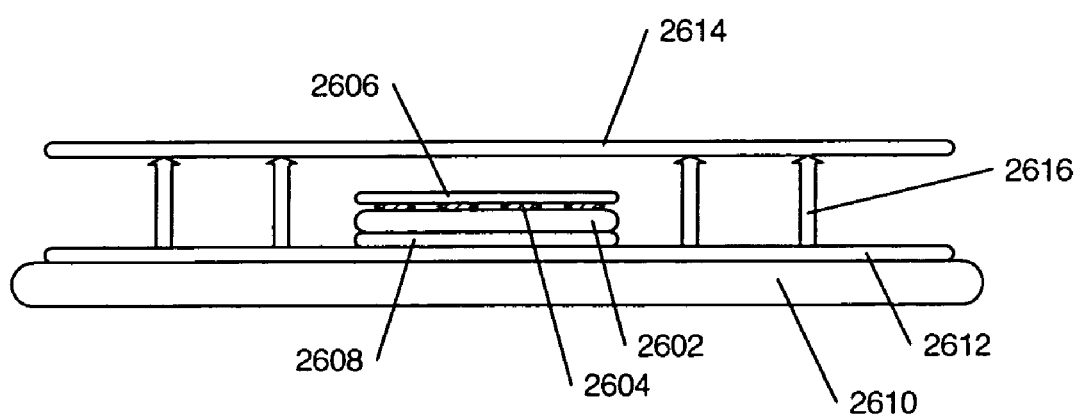
FIG. 26 is a cross-sectional, side view of the wound dressing of FIG. 25, along section lines 26-26, in accordance with an example embodiment.

FIG. 26 is a cross-sectional, side view of the wound dressing of FIG. 25, along section lines 26-26, in accordance with an example embodiment. The dressing may include a substrate 2602, galvanic reservoirs 2604, a tissue contacting layer 2606, a fluid absorbing layer 2608, and a securing mechanism, which may include a structural layer 2610 and an adhesive coating 2612. In addition, a removable liner sheet 2614 may be included with the dressing, to protect the adhesive coating 2612 and tissue contacting layer 2606 from physical and/or environmental damage or degradation, prior to application of the dressing to an area of target tissue. Removable liner sheet 2614 may be removed, as indicated by arrows 2616, prior to use, and adhesive coating 2612 may function to hold a top surface of tissue contacting layer 2606 in a fixed position with respect to an area of target tissue (e.g., against an area of target tissue). In an alternate embodiment, tissue contacting layer 2606 may be excluded, and adhesive coating 2612 may function to hold a top surface of substrate 2602 in a fixed position with respect to the area of target tissue.

During the period of application of the dressing to an area of target tissue, various fluids (e.g., conductive materials and/or wound exudation fluids) may pass through and/or around tissue contacting layer 2606 and substrate 2602 to be absorbed within fluid absorbing layer 2608. In alternate embodiments, fluid absorbing layer 2608 may be excluded from the dressing, or may be positioned above substrate 2602. In still another alternate embodiment, substrate 2602 may include fluid absorbing materials, and thus may function as a fluid absorbing layer.

The dressings illustrated in FIGS. 25 and 26 may be "activated" in one or more of several ways. In an embodiment, activation occurs when a conductive material is located between the reservoirs (e.g., reservoirs 2504, 2506, 2604) such that electrical communication and/or ionic communication may occur between the reservoirs through the conductive material. When a conductive material is between the dissimilar galvanic reservoirs, currents may be produced proximate to a surface of substrate 2602. In various embodiments, these currents may have therapeutic effects, as will be described later.

The conductive material may be proximate to the target tissue area, and/or the conductive material may be applied to the dressing. For example, in an embodiment, wound exudation fluid, blood, and/or other biologic fluids or materials proximate to the area of target tissue may function as an activation material when it is proximate to the reservoirs. In other embodiments, an activation material may be provided with the dressing. For example, an activation material may be included within an activation material reservoir, which may be selectively opened or broken to release an activation material onto the dressing and/or onto a surface of the target tissue area. Alternatively, an activation material may be provided as a solid, semi-solid, liquid, or gaseous material that may otherwise be applied to the dressing and/or an area of target tissue.

Figure 27:
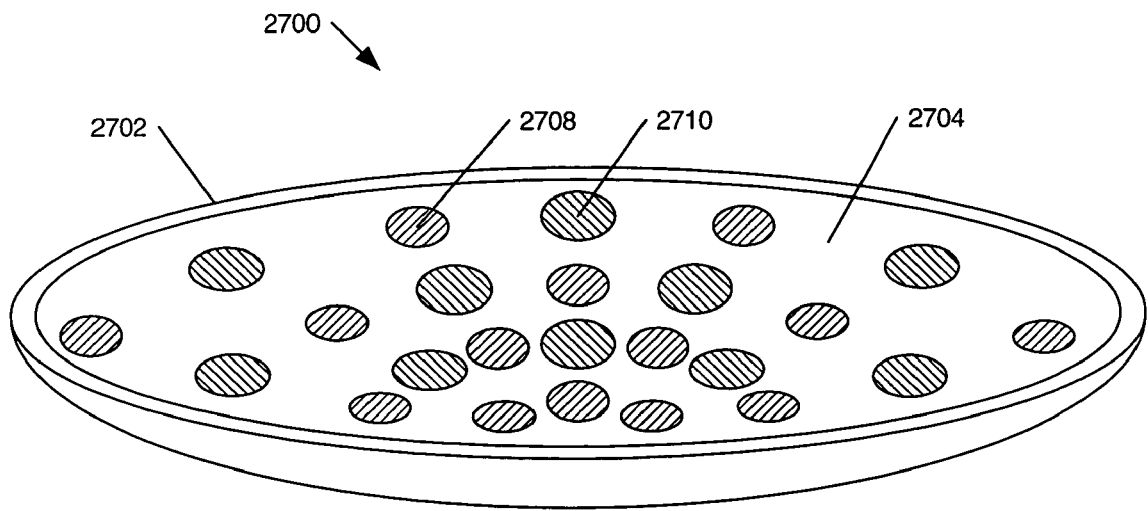
FIG. 27 is a perspective view of an eye contacting device, in accordance with an example embodiment.

FIG. 27 is a perspective view of an eye contacting device 2700, in accordance with an example embodiment. Device 2700 may include a substrate 2702 having an eye facing surface 2704. In an embodiment, first galvanic reservoirs 2708 and second, dissimilar galvanic reservoirs 2710 may be joined with substrate 2702. Although particular numbers, shapes, sizes, and relative orientations of reservoirs are illustrated in FIG. 27, it is to be understood that the numbers, shapes, sizes, and relative orientations may differ, in other embodiments. In some embodiments, reservoirs may be distributed relatively evenly across an eye facing surface. In other embodiments, reservoirs may be distributed unevenly and/or may only be located across one or more portions of the eye facing surface. For example, but not by way of limitation, in an embodiment, reservoirs may be distributed around a periphery of the eye facing surface, and few or no reservoirs may be located in a central area of the eye facing surface.

Substrate 2702 may be formed from soft and/or rigid materials. For example, but not by way of limitation, substrate 2702 may include one or more of electroglas, polymethyl methacrylate (PMMA), rigid gas permeable materials (e.g., silicone-acrylate materials, fluoro-silicone acrylate materials, rigid silicone-hydrogel materials,), soft silicone hydrogel materials (e.g., co-polymers of 2-hydroxyethyl methacrylate (HEMA), N-vinyl-2-pyrrolidone (NVP), methyl methacrylate (MMA)), hyper-oxygen transmissible materials, and/or other materials. In an embodiment, substrate 2702 is substantially transparent. Substrate 2702 may or may not provide for optical correction of refractive eye problems, in various embodiments.

In an embodiment, substrate 2702 is substantially shaped to contour to a surface of an eye, and eye facing surface 2704 is substantially concave. For example, substrate 2702 may be substantially contact-lens shaped. During use, eye facing surface 2704 may be brought into contact with a cornea of an eye. Eye fluids (e.g., tears) may function as an activation material. Accordingly, when the eye fluids contact galvanic reservoirs 2708, 2710, currents may be produced across the eye facing surface 2704. In various embodiments, these currents may have therapeutic effects. For example, but not by way of limitation, eye contacting devices of various embodiments may be applied to the cornea to provide one or more of the following therapeutic effects: 1) reduction in bacterial binding to the cornea surface; 2) reduction in the severity or rate of degeneration caused by cataracts; 3) treatment of iritis, ocular melanoma, Sjogren's syndrome, and/or uveitis; 4) modulating the induction of cellular apoptosis for treatment of altered corneal cell growth (e.g., cataracts); and/or 5) facilitating healing after eye surgery (e.g., cornea transplant, refractive eye surgery).

Figure 28:
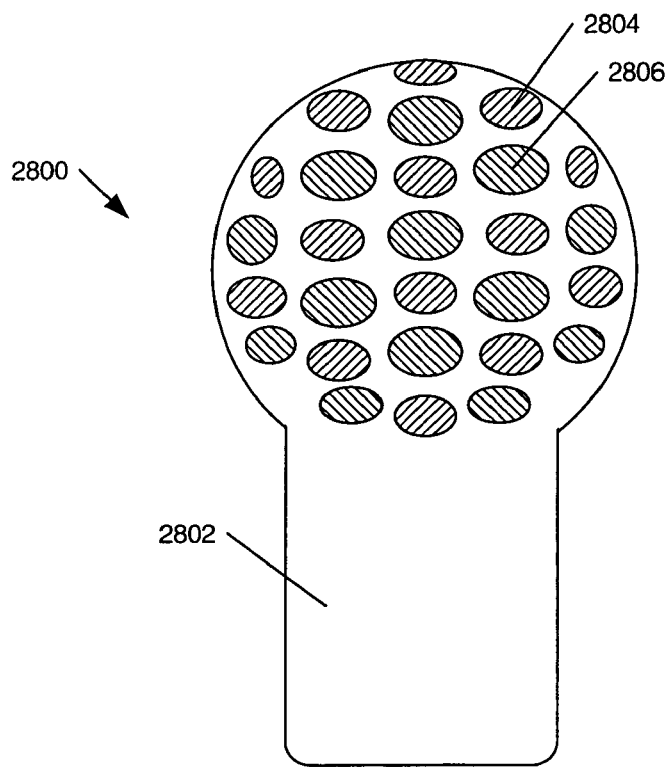
FIG. 28 is a perspective view of an internal prosthetic device, in accordance with an example embodiment.

FIG. 28 is a perspective view of an internal prosthetic device 2800, in accordance with an example embodiment. Device 2800 may include a substrate 2802 having a tissue facing surface 2804. In an embodiment, first galvanic reservoirs 2808 and second, dissimilar galvanic reservoirs 2810 may be joined with substrate 2802. Although particular numbers, shapes, sizes, and relative orientations of reservoirs are illustrated in FIG. 28, it is to be understood that the numbers, shapes, sizes, and relative orientations may differ, in other embodiments. Further, although the substrate 2802 is shown as having a particular form, substrate 2802 may have significantly different forms, in other embodiments.

Substrate 2802 may be formed from one or more solid, semi-solid, flexible, and/or rigid materials. For example, but not by way of limitation, substrate 2802 may include one or more of coated metals or alloys (e.g., titanium, stainless steel, cobalt chrome), plastics (e.g., polyethylene), ceramics, silicone, and/or other materials. In an embodiment, substrate 2802 is substantially non-soluble. Accordingly, device 2800 may retain its form for a long period of time. In alternate embodiments, substrate 2802 may be substantially soluble (e.g., bioabsorbable).

For example, but not by way of limitation, an internal prosthetic device that incorporates an embodiment of the inventive subject matter may form a portion of a replacement prosthesis for a hip, knee, shoulder, elbow, wrist, ankle, vertebrae, disc, cartilage, bone, a hard cosmetic implant (e.g., cheek, chin, or other implant), and/or a breast implant or other soft cosmetic implant (e.g., a breast, calf, pectoral, or other implant). A prosthetic device that incorporates an embodiment of the inventive subject matter may be substantially solid or may have one or more hollow portions. In an embodiment, a hollow prosthetic device may be filled with fluid or another substance (e.g., saline, silicone gel).

A prosthetic device, such as device 2800, may be installed in an interior portion of a body (e.g., press-fit, cemented, inserted into a cavity, or other). During and after installation, tissue facing surface 2804 may come into contact with tissue proximate to the prosthetic device. Bodily fluids and/or bodily tissue (e.g., biologic activation materials) may function as an activation material. Accordingly, when the biologic activation material contacts galvanic reservoirs 2808, 2810, currents may be produced across the tissue facing surface 2804. In various embodiments, these currents may have therapeutic effects. For example, but not by way of limitation, prosthetic devices of various embodiments may be inserted within a body, and may provide one or more of the following therapeutic effects: 1) reduction in infections (e.g., bacterial infections and/or mycobacterial infections) and/or inflammation of tissue proximate to the prosthesis ("proximate tissue"); 2) stimulation of generation of proximate tissue (e.g., new bone); and/or 3) facilitating healing of proximate tissue.

Figure 29:
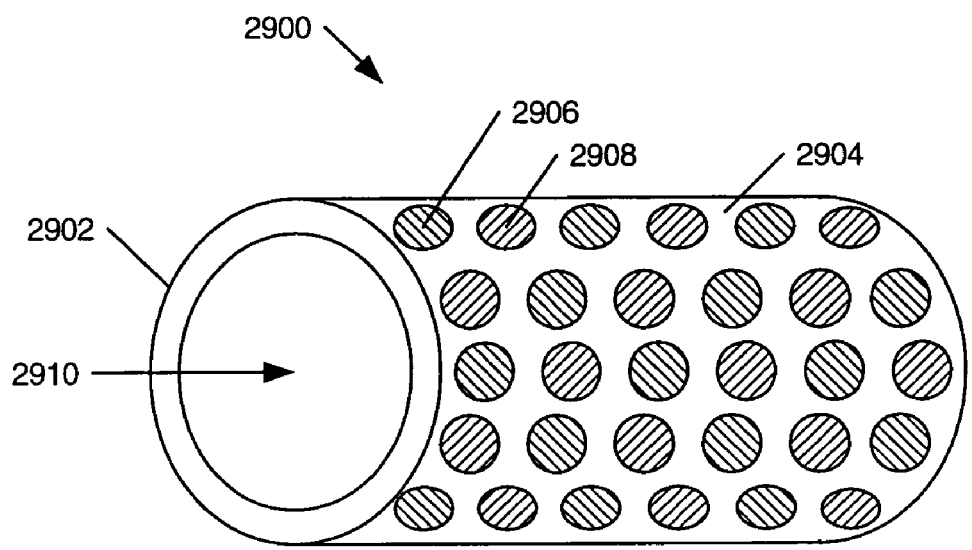
FIG. 29 is a perspective view of an ear canal insert, in accordance with an example embodiment.

FIG. 29 is a perspective view of an ear canal insert 2900, in accordance with an example embodiment. Insert 2900 may include a substrate 2902 having an ear canal facing surface 2904. In an embodiment, first galvanic reservoirs 2906 and second, dissimilar galvanic reservoirs 2908 may be joined with substrate 2902. Although particular numbers, shapes, sizes, and relative orientations of reservoirs are illustrated in FIG. 29, it is to be understood that the numbers, shapes, sizes, and relative orientations may differ, in other embodiments. Further, although the substrate 2902 is shown as having a particular form, substrate 2902 may have significantly different forms, in other embodiments.

Substrate 2902 may be formed from one or more solid, semi-solid, flexible, and/or rigid materials. For example, but not by way of limitation, substrate 2902 may include one or more of a polymer, polyurethane foam, silicone, and/or other materials.

In an embodiment, substrate 2902 is substantially shaped to contour to an ear canal. In an embodiment, substrate 2902 may include an opening 2910 that extends co-axially through the center of substrate 2902. In an embodiment, opening 2910 may enable fluids to pass from an interior portion of an ear canal to an exterior of the ear canal. In an alternate embodiment, substrate 2902 may be substantially solid, and may not include an opening.

An insert, such as insert 2900, may be installed in an ear canal. Before, during, and/or after installation, tissue facing surface 2904 may come into contact with tissue within the ear canal, such as the walls of the ear canal and the ear drum. An activation material may be applied to the insert before, during, and/or after installation. In addition, bodily fluids and/or bodily tissue (e.g., biologic activation materials) may function as an activation material. When the activation material contacts galvanic reservoirs 2906, 2908, currents may be produced across the tissue facing surface 2904. In various embodiments, these currents may have therapeutic effects. For example, but not by way of limitation, inserts of various embodiments may be inserted within an ear canal, and may provide one or more of the following therapeutic effects: 1) reduction in infections (e.g., bacterial infections and/or mycobacterial infections) and/or inflammation of tissue proximate to the insert ("proximate tissue"); 2) stimulation of generation of proximate tissue (e.g., new bone); and/or 3) facilitating healing of proximate tissue.

Figure 30:
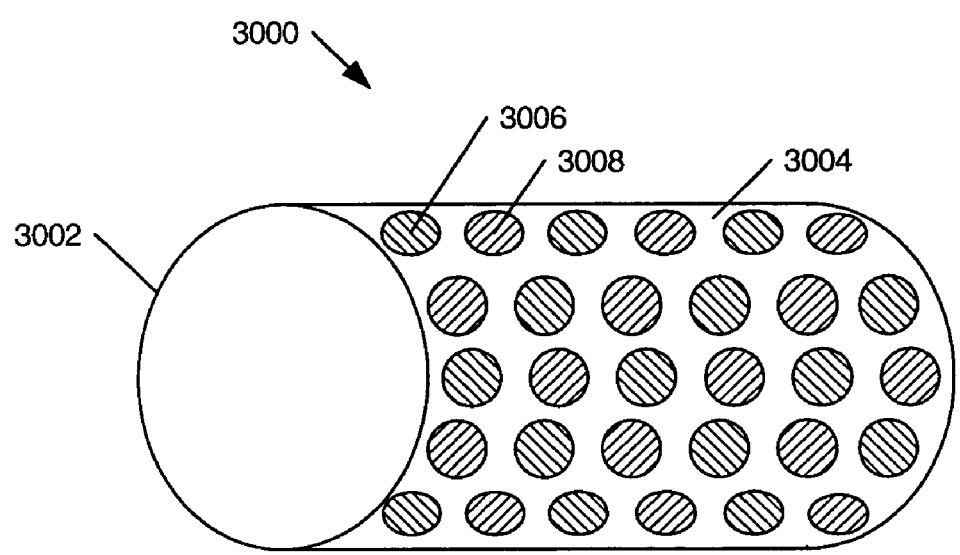
FIG. 30 is a perspective view of a tampon, in accordance with an example embodiment.

FIG. 30 is a perspective view of an intra-vaginal device 3000 (e.g., a tampon, pessary, sponge, diaphragm, or other device), in accordance with an example embodiment. Device 3000 may include a substrate 3002 having an vaginal wall facing surface 3004. In an embodiment, first galvanic reservoirs 3006 and second, dissimilar galvanic reservoirs 3008 may be joined with substrate 3002. Although particular numbers, shapes, sizes, and relative orientations of reservoirs are illustrated in FIG. 30, it is to be understood that the numbers, shapes, sizes, and relative orientations may differ, in other embodiments. Further, an intra-vaginal device may have one or more additional structural elements not illustrated in FIG. 30, and/or may have a substantially different shape.

Substrate 3002 may be formed from one or more flexible materials. For example, but not by way of limitation, substrate 3002 may include one or more of cotton, rayon, other cellulose fiber-based materials, and/or other materials. Substrate 3002 may be substantially shaped to contour to a surface within a vaginal area.

An intra-vaginal device, such as device 3000, may be installed into a vaginal canal. Before, during, and/or after installation, tissue facing surface 3004 may come into contact with vaginal wall tissue and/or cervical tissue. Bodily fluids and/or bodily tissue (e.g., biologic activation materials) may function as an activation material. When the activation material is located between galvanic reservoirs 3006, 3008, currents may be produced across the tissue facing surface 3004. In various embodiments, these currents may have therapeutic effects. For example, but not by way of limitation, tampons of various embodiments may be inserted within a vaginal canal, and may provide one or more of the following therapeutic effects: 1) reduction in infections (e.g., chlamydia, yeast, and/or bacterial infections and/or mycobacterial infections) and/or inflammation of tissue proximate to the insert ("proximate tissue"); 2) treatment of cervical dysplasia; and/or 3) facilitating healing of proximate tissue.

Figure 31:
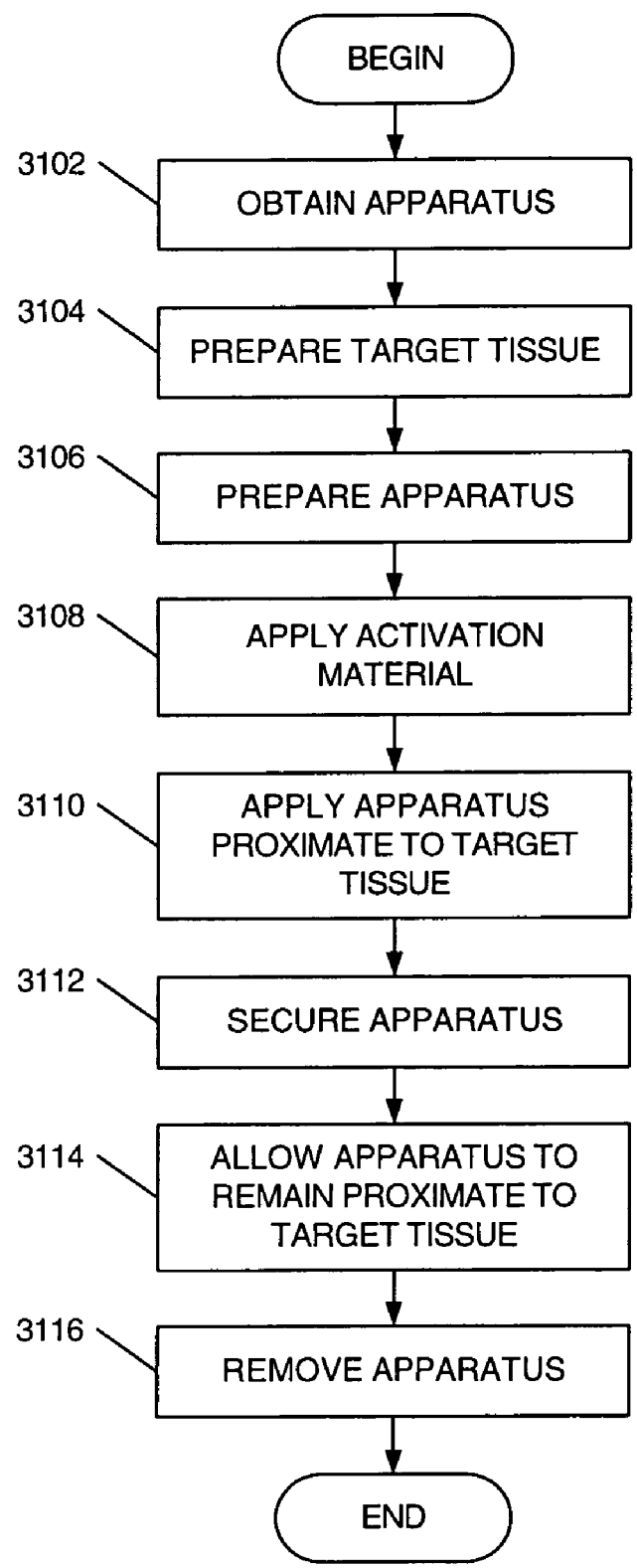
FIG. 31 is a flowchart of a method for applying an apparatus to a target tissue area, in accordance with an example embodiment.

FIG. 31 is a flowchart of a method for applying an apparatus to a target tissue area, in accordance with an example embodiment. In block 3102, an apparatus may be obtained, which includes an embodiment of the inventive subject matter.

In block 3104, an area of target tissue optionally may be prepared for application of the apparatus. Preparation of the target tissue may include one or more processes such as cleaning the area of target tissue, making one or more incisions to expose the area of target tissue, resurfacing the area of target tissue, and/or any of a number of other processes. In an alternate embodiment, no target tissue preparation may be performed.

In block 3106, the apparatus optionally may be prepared for application to a target tissue area. For example, but not by way of limitation, the apparatus may be removed from protective packaging, the apparatus may be cut or torn to size, and/or one or more release liners may be removed from the apparatus.

In block 3108, an activation material optionally may be applied to the apparatus and/or to the target tissue area. For example, but not by way of limitation, a conductive material may be released from an activation material reservoir associated with the apparatus, or another type of activation material associated with the apparatus may be placed in contact with the apparatus and/or the area of target tissue. In alternate embodiments, an activation material may not be applied, and the apparatus may be activated when it comes into contact with activation material proximate to the target tissue area.

In block 3110, the apparatus may be applied proximate to the target tissue area. In an embodiment, application of the apparatus may result in currents between dissimilar reservoirs contacting (e.g., penetrating or contacting the surface of) the target tissue area. Alternatively or in addition, application may result in currents electromotivating therapeutic materials toward the target tissue area. Application of the apparatus may result in additional or different effects, in other embodiments.

In block 3112, the apparatus optionally may be secured to tissue or structures proximate to the target tissue area. The apparatus may be secured using a securing mechanism associated with the apparatus, a securing mechanism distinct from the apparatus, and/or by tissue and/or other structures proximate to the target tissue area.

In block 3114, the apparatus optionally may be allowed to remain in proximity to the target tissue area for a period of time, referred to as a "period of application." A period of application of an apparatus may be shorter than, approximately equal to, or longer than an apparatus' "period of effectiveness." A "period of effectiveness" may be defined, in some embodiments, as a period of time during which an apparatus may or may not perform a beneficial activity (e.g., production of currents, iontophoresis, supply of anti-bacterial or other therapeutic materials, etc.). A period of effectiveness may depend on one or more of several factors, including the materials, material concentrations, and material orientations within the apparatus, the conductive material, ambient conditions (e.g., temperature, target tissue characteristics, etc.), and other factors. In an embodiment, an apparatus may have a period of effectiveness in a range from approximately 1-14 days, although an apparatus may have a period of effectiveness that is longer or shorter than this range, in other embodiments. In an embodiment, the first reservoirs and the second reservoirs are configured to sustain the one or more currents for approximately a pre-determined period of time (e.g., a pre-determined period of effectiveness).

In block 3116, an apparatus optionally may be removed and/or replaced, in an embodiment. In an alternative embodiment, an apparatus may remain in proximity to an area of target tissue indefinitely. The method then ends.

Applications or uses for embodiments of the inventive subject matter may include any one or more of several types of methods of use. For example, but not by way of limitation, the terms "methods of application" or "methods of applying" may include, but are not limited to, one or more of the following:

1) methods of treatment to enhance healing of breached or compromised biologic tissue and/or tissue disorders;
2) methods to apply electricity to an area of biologic tissue to provide therapeutic results;
3) methods to reduce the appearance of a tissue condition;
4) methods to provide therapeutic materials to an area of biologic tissue and/or to a biologic system through an area of biologic tissue;
5) methods to reduce or eliminate infections (e.g., bacterial, mycobacterial, yeast, viral, and/or fungal infections) within an area of biologic tissue and/or within a biologic system;
6) methods to reduce a likelihood for infections (e.g., bacterial, mycobacterial, yeast, viral, and/or fungal infections) within an area of biologic tissue and/or within a biologic system; and/or
7) methods to alter the cellular activity of an area of biologic tissue and/or within a biologic system (e.g., cellular induction, modulation of cellular differentiation and/or de-differentiation, modulation of cellular apoptosis, modulation of cellular morphology, modulation of cellular function, modulation of cellular activity, modulation of cellular chemical activity and/or behavior).

In various embodiments, methods of achieving various affects on biologic tissue and/or biologic systems may include applying embodiments of apparatus to an area of biologic tissue. Embodiments may be applied to biologic tissue and/or fluids selected from a group of tissue types that includes, but is not limited to, skin tissue, epithelial tissue, optic tissue, otic tissue, mucous membrane tissue, connective tissue, muscle tissue, nerve tissue, cerebrospinal fluid, abdominal cavity fluid, and/or other biologic tissue and/or fluids (e.g., bone, organ tissue, etc.). An area of biologic tissue selected for application of an embodiment may include biologic tissue selected from a group that includes, but is not limited to, damaged biologic tissue, inflamed biologic tissue, diseased biologic tissue, infected biologic tissue, healthy biologic tissue, and combinations thereof.

The terms "treat," "treating," and "treatment" may be defined, in some embodiments, as the treatment (e.g., alleviation or elimination of symptoms and/or cure) and/or prevention or inhibition of a condition or disorder of tissue or a biologic system. The terms "condition" and "disorder," may be defined, in some embodiments, as diseases, disorders, and/or characteristics of tissue. The term "enhance healing of" may be defined, in some embodiments, as improving results of healing, reducing scarring during healing, and/or expediting healing.

In various embodiments, methods of application (e.g., embodiments of FIG. 31) may include methods to treat and/or to enhance healing of breached or compromised biologic tissue, where the tissue may include one or more conditions selected from a group that includes, but is not limited to, an infected traumatic lesion, a surgical incision, a lesion, a wound, a cut, a puncture, a rupture, an abrasion, a laceration, a biopsy site, post-laser treated skin, post-chemical peeled skin, a burn, sunburn, frostbite, an ulcer, a bed sore, a rash, contact dermatitis (e.g., from poison ivy/poison oak exposure), an insect bite and/or sting, a snake bite, and an animal bite.

In various embodiments, methods of application (e.g., embodiments of FIG. 31) may include methods to treat and/or to enhance healing of skin, hair, and nail conditions, where the tissue may include-one or more conditions selected from a group that includes, but is not limited to, a bacterial infection, a mycobacterial infection, a yeast infection, a fungal infection, a viral infection, a scar, acne, blisters, a corn, a callus, dermatographia, hives, angioedema, psoriasis, rosacea, scabies, vitiligo, dysplasia, dermatitis (eczema), ecthyma, atopic dermatitis, dyshidrosis, neurodermatitis, athlete's foot, a boil, carbuncles, cellulitis, a cold sore, folliculitis, furunculosis, impetigo, jock itch, molluscum conagiosum, herpes, Mucha-Havermann disease, ringworm, shingles, tinea versicolor, actinic keratosis, a wart, freckles, a mole, unusual pigmentation, lipoma, melanoma, scalp cancer, skin cancer, acanthosis nigricans, bullous pemphigoid, epidermolysis bullosa, icthyosis, pityriasis rosea, granuloma annulare, hidradenitis, lichen nitidus, lichen planus, morphea, scleroderma, pilonidial cysts, pyoderma gangrene, Stevens-Johnson syndrome, hemangioma, sweating, body odor, cercarial dermatitis, an ingrown toenail, and/or a nail fungal infection.

In various embodiments, methods of application (e.g., embodiments of FIG. 31) may include methods to treat and/or to enhance healing of mucosa tissue (e.g., mucous membranes), where the tissue may include one or more conditions selected from a group that includes, but is not limited to, an oral or vaginal yeast infection, a sty, conjunctivitis, gingivitis, oral cancer, a cancer sore, and/or cervical cancer.

In various embodiments, methods of application (e.g., embodiments of FIG. 31) may include methods to treat and/or to enhance healing of ear and/or eye tissue, where the tissue may include one or more conditions selected from a group that includes, but is not limited to, conjunctivitis, a sty, cataracts, iritis, ocular melanoma, Sjogren's syndrome, uveitis, an ear infection, a ruptured ear drum, and/or tissue compromised by cornea transplant, refractive eye surgery or ear surgery.

In various embodiments, methods of application (e.g., embodiments of FIG. 31) may include methods to reduce a likelihood of, prevent, and/or reduce infection of tissue proximate to an apparatus, including but not limited to, a wound dressing, a contact lens, a replacement prosthesis for a hip, knee, shoulder, elbow, wrist, ankle, vertebrae, disc, cartilage, bone, a hard cosmetic implant (e.g., cheek, chin, or other implant), a breast implant or other soft cosmetic implant (e.g., a breast, calf, pectoral, or other implant), an ear canal insert, a stent, a tampon, diaphragm, sponge, intra-uterine device, pessary, a urinary tract catheter, an intravenous catheter, a tracheal tube, a gastrointestinal feeding tube, a screw, a clamp, a surgical instrument, mask, diagnostic device, a gown, garment, glove, sock, head covering, a wipe, and/or a towel.

In various embodiments, methods of application (e.g., embodiments of FIG. 31) may include methods to reduce or to reverse the appearance of various skin characteristics, including but not limited to, reducing or reversing skin pigmentation, scars, hair loss, hair growth, uneven skin texture, non-optimal skin firmness, non-optimal skin elasticity, apparent skin vasculature, dark eye circles, cellulite, non-optimal skin shine, tumors, and wrinkles. The term "to reduce" may be defined, in some embodiments, as to make less apparent to the eye. The term "to reverse" may be defined, in some embodiments, as to transform to a previous condition.

Application of an embodiment of the invention to an area of target tissue may or may not produce one or more beneficial results, including but not limited to:
  a) stimulation of fibroplasia (e.g., regeneration of connective tissue);
  b) collagen remodeling (e.g., reforming of collagen fibrils);
  c) stimulation of neoangiogenesis (e.g., regenerating blood supply to tissue);

d) anti-microbial action (e.g., attraction of microbes toward a reservoir, and neutralization of the microbes through contact with reservoir material);

e) providing an electromotive force to drive one or more materials (e.g., silver and/or zinc) toward and/or into an area of target tissue (e.g., iontophoresis), which may or may not have an effect of killing microbes, and/or moving or attracting electrically charged healing cells;

f) electrically attracting microbes proximate to or within an area of target tissue to a reservoir, and when the reservoir includes anti-microbial materials, killing the attracted microbes;

g) stimulating biologic currents normally produced at tissue injury sites;

h) wound contraction;

i) providing wound healing stimulus across an entire wound surface by providing current over the wound surface (e.g., simulating a current of injury usually found around a periphery of a wound to an entire wound surface);

j) alteration of capillary permeability;

k) cellular migration;

l) changing cellular activity from hypoactive or hyperactive to normal (e.g., in a state of homeostasis); and/or m) modifying cellular induction, modulation of cellular differentiation and/or de-differentiation, modulation of cellular apoptosis, modulation of cellular morphology, modulation of cellular function, modulation of cellular activity, modulation of cellular chemical activity and/or behavior.

EXAMPLE

In vivo Human Study

An in vivo study was conducted in a human volunteer using an apparatus in accordance with an embodiment. The study was performed using a 63 year old male physician volunteer with diabetes mellitus and polio. The male subject had his great toe amputated on his left foot approximately four years prior to the study (circa 2000). Post-operatively he sustained a burn of his foot with injuries to the great toe amputation stump, and also to the second, third, and fourth toes (i.e., the "target tissue"). The injuries became infected. The target tissue failed to heal after approximately four years of conventional medical treatments. Approximately one month prior to the study, a proximal amputation was recommended by the subject's physician. Rather than receive the amputation, the subject opted to volunteer for the in vivo study using apparatus in accordance with an embodiment.

Figure 32:
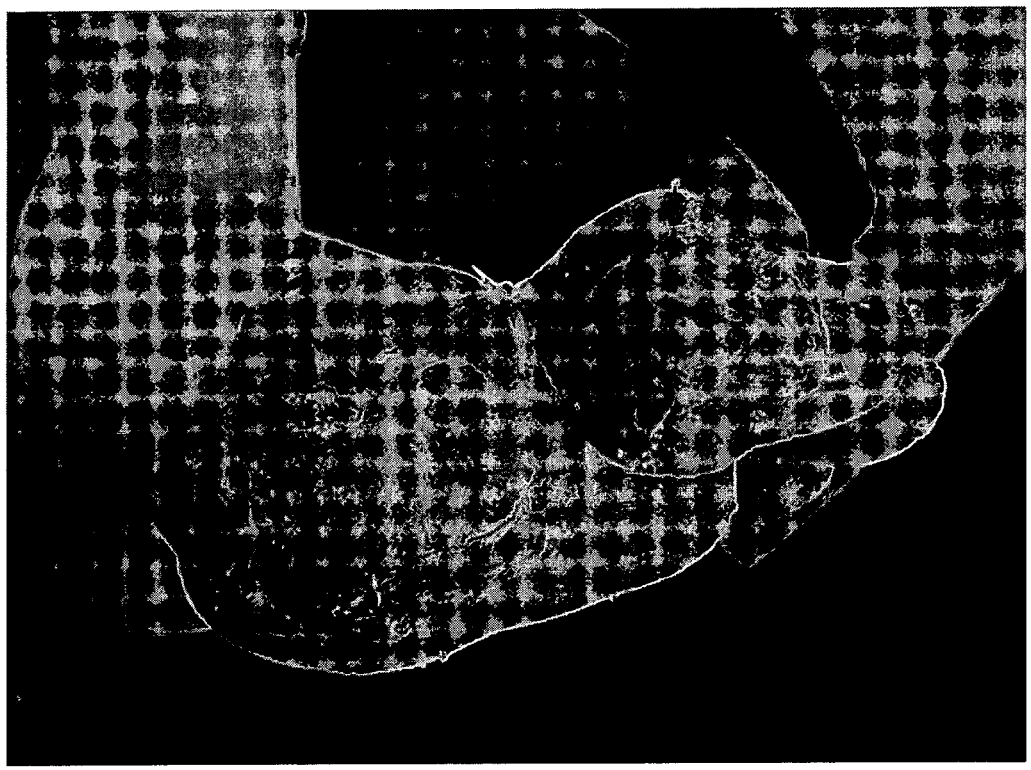
FIGS. 32 and 33 are photographic images of an area of target tissue prior to application of an embodiment of an apparatus.
Figure 33:
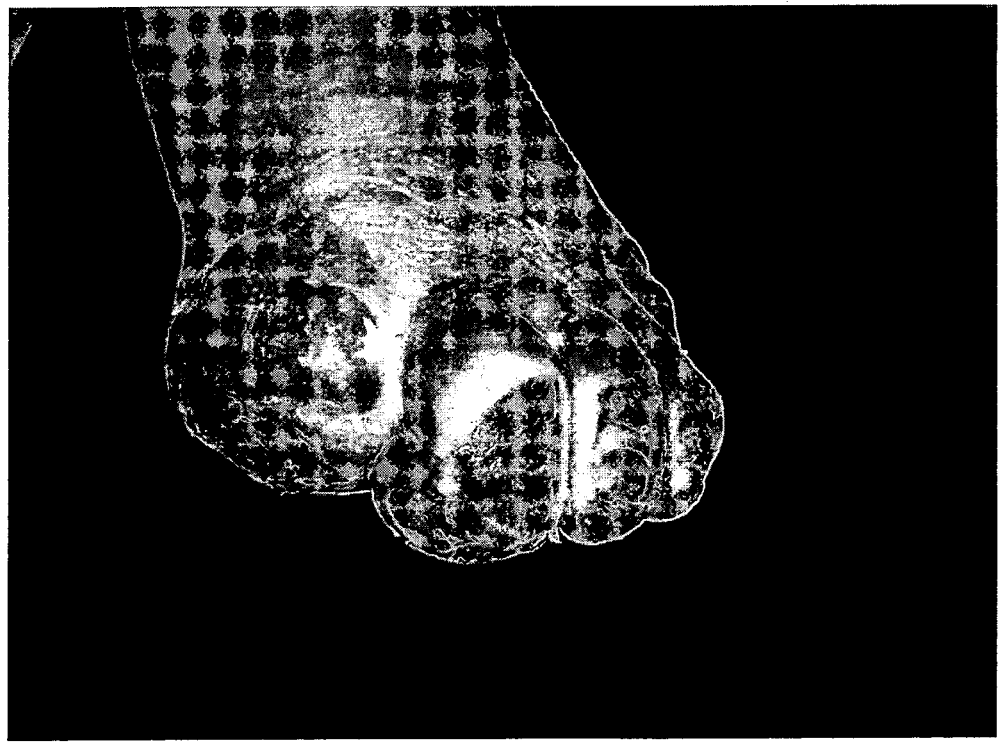

FIGS. 32 and 33 are photographic images of an area of target tissue prior to application of an embodiment of an apparatus. The target tissue was located on the subject's left foot, and the photographic images are a front-view and a top view, respectively, of the subject's foot. The target tissue included a primary wound in proximity to the great toe amputation site. FIG. 32 is photographic images of an area of target tissue prior to application of an embodiment of the device. The primary wound had exposed sub-dermal tissue with an area of approximately 4.2 cm$^2$. There was no dermal or epidermal coverage across the primary wound. The peripheral margin of the wound was necrotic and the metatarsal head was exposed at the amputation wound site. The tissue across the primary wound was friable. The primary wound produced exuberant exudate. Cultures of the primary wound grew methicillin resistant staphylococcus aureus and enterococcus faecalis. The target tissue also included secondary wounds on the second, third, and fourth toes.

The study was conducted over a 49-day period. During the study, no conventional treatments were utilized. An embodiment of a medical battery apparatus was applied directly to the target tissue at the onset of the study (e.g., on day 1). The apparatus was moistened with water, laid directly on the wound, and secured with cotton roller-gauze. The apparatus was removed prior to showering and promptly re-applied thereafter. The apparatus was replaced approximately once per week.

The apparatus included a substrate formed from woven polyester fabric. A first pattern of reservoirs was positioned on a primary surface of the substrate. The first reservoir material included a binder mixed with high-purity silver crystals, which was screen printed onto the primary surface and cured. A second pattern of reservoirs was positioned on the primary surface interleaved with the first pattern. The second reservoir material included a binder mixed with high-purity zinc crystals, which was screen printed onto the primary surface and cured. The first reservoirs were circular, and had diameters of approximately 1 mm. The second reservoirs were circular, and had diameters of approximately 0.5 mm. Spacings of approximately 1 mm were present between nearest adjacent first reservoirs and second reservoirs, across the primary surface. The apparatus was activated by water and contact with the wound exudate.

Within four days, observable changes were evident in the target tissue, including resolution of the infection. After ten days of application, observations were made that the wounds were significantly covered with healing tissue, and the previously-exposed bone in the great toe amputation site was covered with tissue. An observation was made that the tissue was not only healing from the peripheral margins of the wounds, but was also healing over the entire wound surface.

Figure 34:
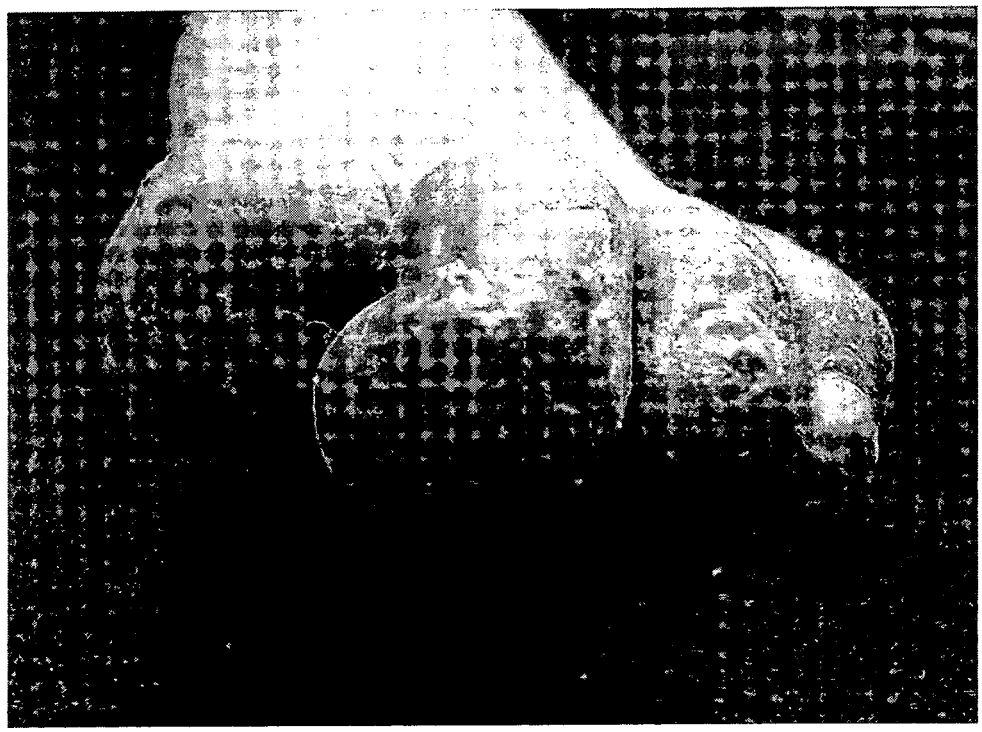
FIGS. 34 and 35 are photographic images of an area of target tissue after application of an embodiment of an apparatus for a period of 35 days.
Figure 35:

FIGS. 34 and 35 are photographic images of an area of target tissue after application of an embodiment of an apparatus for a period of 35 days. After 35 days of application, observations were made that the open wounds had experienced significant healing, and were filled with thick, mature tissue (e.g., tough, mature tissue that could not be disrupted from the wound surface). Healing progressed through the course of the study. The study was terminated after 49 days when the wounds were completely healed.

Thus, various embodiments of medical apparatus and methods of use and manufacture have been described. The foregoing description of specific embodiments reveals the general nature of the inventive subject matter sufficiently that others can, by applying current knowledge, readily modify and/or adapt it for various applications without departing from the general concept. Therefore, such adaptations and modifications are within the meaning and range of equivalents of the disclosed embodiments.

The phraseology or terminology employed herein is for the purpose of description and not of limitation. Accordingly, the inventive subject matter embraces all such alternatives, modifications, equivalents and variations as fall within the spirit and broad scope of the appended claims.

What is claimed is:

1. A method for treating an area of biologic tissue, the method comprising:

determining a size of the area of biologic tissue for treatment;

selecting an apparatus that includes a substrate having an active surface that is at least as large as the size of the area of biologic tissue, the active surface having a first pattern of multiple first discrete reservoirs interleaved with a second pattern of multiple second discrete reservoirs to form an alternating arrangement of the first and second reservoirs on the active surface of the substrate, the first reservoirs including a reducing agent, and the second reservoirs including an oxidizing agent;

applying the apparatus in contact with the area of biologic tissue;

securing the apparatus to the area of biologic tissue to remain in contact with the area of biologic tissue for a period of time; and producing, in response to the applying operation, redox reactions between adjacent ones of first reservoir surfaces of the first reservoirs and the second reservoir surfaces of the second reservoirs on the active surface to provide current between the first and second reservoirs capable of penetrating the area of biologic tissue to treat the area of biologic tissue.

2. A method as claimed in claim 1 further comprising:

activating the active surface by positioning an activation material between the active surface and the area of biologic tissue, wherein the currents are generated between the adjacent ones of the first and second discrete reservoirs in the presence of the activation material.

3. The method as claimed in claim 1 wherein:

each of the first discrete reservoirs exhibits a first diameter of approximately 2 mm;

each of the second discrete reservoirs exhibits a second diameter of approximately 1 mm; and a lateral spacing between corresponding perimeters of adjacent ones of the first discrete reservoirs and the second discrete reservoirs is in a range of approximately 0.5 - 2.0 mm so that the first discrete reservoirs do not physically contact the second discrete reservoirs.

4. The method as claimed in claim 1 wherein the reducing agent includes silver, the oxidizing agent includes zinc, the amount of zinc in each of the multiple second discrete reservoirs being approximately half of the amount of silver in each of the multiple first discrete reservoirs, and the method further comprises:

upon depletion of the zinc in the multiple second discrete reservoirs in response to the redox reaction produced between the first reservoir surfaces and the second reservoir surfaces, retaining the apparatus in contact with the area of biologic tissue to provide anti-microbial effects of a remaining portion of the silver in the area of biologic tissue.

5. The method as claimed in claim 1 wherein each of the multiple first discrete reservoirs includes a binder material attached with the reducing agent, each of the multiple second discrete reservoirs includes the binder material attached with the oxidizing agent, and the method further comprises:

degrading the binder material in the multiple first and second discrete reservoirs in the presence of an activation material;

exposing, in response the degrading operation, the reducing agent to the first reservoir surfaces of the first discrete reservoirs; and exposing, in response the degrading operation, the oxidizing agent to the second reservoir surfaces of the second discrete reservoirs.

\* \* \* \* \*